(12) United States Patent
Bissantz et al.

(10) Patent No.: US 8,293,770 B2
(45) Date of Patent: Oct. 23, 2012

(54) PYRROLIDINE DERIVATIVES AS NK-3 RECEPTOR ANTAGONISTS

(75) Inventors: Caterina Bissantz, Village-Neuf (FR); Philippe Jablonski, Steinbrunn-le-Haut (FR); Henner Knust, Rheinfelden (DE); Matthias Nettekoven, Grenzach-Wyhlen (DE); Angelique Patiny-Adam, Rosenau (FR); Hasane Ratni, Habsheim (FR); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 303 days.

(21) Appl. No.: 12/572,282

(22) Filed: Oct. 2, 2009

(65) Prior Publication Data

US 2010/0168088 A1 Jul. 1, 2010

(30) Foreign Application Priority Data

Oct. 9, 2008 (EP) .................................... 08166184

(51) Int. Cl.
| | |
|---|---|
| A61K 31/40 | (2006.01) |
| A61K 31/44 | (2006.01) |
| C07D 207/04 | (2006.01) |
| C07D 401/02 | (2006.01) |

(52) U.S. Cl. ...................... 514/340; 548/530; 546/276.4; 514/423

(58) Field of Classification Search ............... 546/268.1, 546/276.4; 548/530; 514/336, 340, 408, 514/423

See application file for complete search history.

(56) References Cited

U.S. PATENT DOCUMENTS

| | | | | |
|---|---|---|---|---|
| 7,812,021 | B2 * | 10/2010 | Jablonski et al. | ........... 514/235.5 |
| 8,022,099 | B2 * | 9/2011 | Bissantz et al. | ............... 514/426 |
| 2006/0149062 | A1 | 7/2006 | Jolidon et al. | |

FOREIGN PATENT DOCUMENTS

| | | |
|---|---|---|
| WO | WO 2005/110987 | 11/2005 |
| WO | WO 2006/072436 | 7/2006 |

OTHER PUBLICATIONS

Written Opinion of the Internal Examining Authority dated Oct. 1, 2010.
Mackenzie et al., J. of Medicinal Chemistry, 45:24 5356-5377 XP008059050.
Albert J. S. et al, Expert Opinion on Therapeutic Patents, 16:7, 925-937 (2006) XP002489687.
Maynard, G.D. et al., Bioorganic & Medicinal Chemistry Letters, 7:22 (1997) 2819 XP004136537.
Tooney et al., Neurosci. Letters, 2000, vol. 283 pp. 185-188.
Giardina et al., Exp. Opin. Ther. Patents, 2000, vol. 19 pp. 939-960.
Jung et al., Neuroscience, 1996 vol. 74 pp. 403-414.
Marco et al., Neuropeptides, 1998, vol. 32, pp. 481-488.
Kamali, F., Current Opinion in Investigational Drugs, 2001, vol. 2(7) pp. 950-956.
Pitt et al., Bioorg. Med./Chem. Lett. 2004 vol. 14, pp. 4585-4589.

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to a compound of formula I

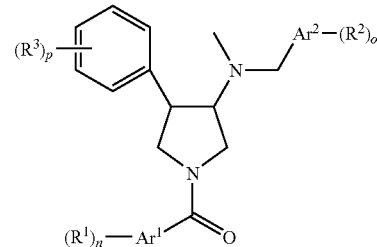

wherein
$Ar^1$, $Ar^2$, $R^1$, $R^2$, $R^3$, n, o, and p are as described herein
or to a pharmaceutically active salt, to all stereoisomeric forms, including individual diastereoisomers and enantiomers as well as to racemic and non-racemic mixtures thereof. Compounds of the invention are high potential NK-3 receptor antagonists for the treatment of depression, pain, psychosis, Parkinson's disease, schizophrenia, anxiety and attention deficit hyperactivity disorder (ADHD).

7 Claims, No Drawings

PYRROLIDINE DERIVATIVES AS NK-3 RECEPTOR ANTAGONISTS

PRIORITY TO RELATED APPLICATIONS

This application claims the benefit of European Patent Application No. 08166184.5, field Oct. 9, 2008, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001,2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.). Objects of the present invention are novel compounds of formula I, their manufacture, medicaments based on a compound in accordance with the invention and their production as well as the use of compounds of formula I in the control or prevention of illnesses such as depression, pain, bipolar disorders, psychosis, Parkinson's disease, schizophrenia, anxiety and attention deficit hyperactivity disorder (ADHD).

SUMMARY OF THE INVENTION

The present invention provides a compound of formula I

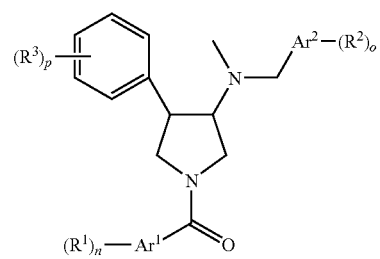

wherein
$Ar^1$ is aryl or heteroaryl;
$Ar^2$ is aryl or heteroaryl;
$R^1$ is hydrogen, halogen, hydroxy, lower alkyl, lower alkoxy, lower alkyl substituted by halogen, lower alkoxy substituted by halogen, S-lower alkyl, —$S(O)_2$-lower alkyl, —$S(O)_2$-di-lower alkyl amino, cyano, amino, mono or di-lower alkyl amino, C(O)-lower alkyl, NHC(O)-lower alkyl, cycloalkyl, heterocyclyl, or heteroaryl optionally substituted by lower alkyl;
$R^2$ is hydrogen, halogen, lower alkyl, lower alkoxy, lower alkyl substituted by halogen or cyano;
$R^3$ is hydrogen, halogen, lower alkyl or lower alkyl substituted by halogen;
n is 1, 2 or 3; wherein when n is 2 or 3, each $R^1$ is the same or different;
o is 1, 2 or 3; wherein when o is 2 or 3, each $R^2$ is the same or different; and
p is 1, 2 or 3; wherein when p is 2 or 3, each $R^4$ is the same or different;
or a pharmaceutically active salt thereof.

The invention includes all stereoisomeric forms, including individual diastereoisomers and enantiomers of the compound of formula (I) as well as racemic and non-racemic mixtures thereof.

Compounds of the invention are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes a lower alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "halogen" denotes chlorine, iodine, fluorine and bromine.

The term "lower alkoxy" denotes an O—R group wherein R is lower alkyl as defined above.

The term "lower alkoxy substituted by halogen" denotes a lower alkoxy group as defined above, wherein at least one hydrogen atom is replaced by halogen, for example, —$OCF_3$, —$OCHF_2$, —$OCH_2F$, —$OCH_2CF_3$, —$OCH_2CH_2CF_3$, —$OCH_2CF_2CF_3$ and the like.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is phenyl.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom selected from N, O and S, for example quinoxalinyl, dihydroisoquinolinyl, pyrazin-2-yl, pyrazol-1-yl, 2,4-dihydro-pyrazol-3-one, pyridinyl, isoxazolyl, benzo[1,3] dioxol, pyridyl, pyrimidin-4-yl, pyrimidin-5-yl, benzotriazol-5-yl, benzoimidazol-5-yl, [1,3,4]-oxadiazol-2-yl, [1,2,4] triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred heteroaryl group is pyridine-2, 3 or 4-yl.

The term heterocyclyl denotes a five or six membered nonaromatic ring, containing one or two heteroatoms selected from N, S and O, for example the following groups: morpholinyl, 1,1-dioxo-1-6-isothiazolidin-2-yl, piperazinyl, optionally substituted in 1 position by carboxylic acid tert-butyl ester or is 1,1,-dioxo-1-6-thiomorpholin-4-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Compounds of formula I, wherein $Ar^1$ is aryl and $Ar^2$ is phenyl are preferred.

Preferred specific compounds are the following:

4-{(3SR,4RS)-3-(3,4-dichloro-phenyl)-4-[(3-fluoro-4-trifluoromethyl-benzyl)-methyl-amino]-pyrrolidine-1-carbonyl}-benzonitrile;

3-{(3SR,4RS)-3-(3,4-dichloro-phenyl)-4-[(3-fluoro-4-trifluoromethyl-benzyl)-methyl-amino]-pyrrolidine-1-carbonyl}-benzonitrile;

4-({[(3RS,4SR)-1-(4-cyano-benzoyl)-4-(3,4-dichloro-phenyl)-pyrrolidin-3-yl]-methyl-amino}-methyl)-2-fluoro-benzonitrile;

4-{(3SR,4RS)-3-(3,4-dichloro-phenyl)-4-[(3-fluoro-4-trifluoromethyl-benzyl)-methyl-amino]-pyrrolidine-1-carbonyl}-3-fluoro-benzonitrile;

{(3SR,4RS)-3-(3,4-dichloro-phenyl)-4-[(3-fluoro-4-trifluoromethyl-benzyl)-methyl-amino]-pyrrolidin-1-yl}-(2-fluoro-5-methanesulfonyl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-methanesulfonyl-phenyl)-methanone;

4-{(3SR,4RS)-3-(3,4-dichloro-phenyl)-4-[(3-fluoro-4-trifluoromethyl-benzyl)-methyl-amino]-pyrrolidine-1-carbonyl}-2-methyl-benzonitrile;

1-(4-{(3SR,4RS)-3-(3,4-dichloro-phenyl)-4-[(3-fluoro-4-trifluoromethyl-benzyl)-methyl-amino]-pyrrolidine-1-carbonyl}-phenyl)-ethanone;

{(3SR,4RS)-3-(3,4-dichloro-phenyl)-4-[(3-fluoro-4-trifluoromethyl-benzyl)-methyl-amino]-pyrrolidin-1-yl}-(4-morpholin-4-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-[1,2,4]triazol-1-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-imidazol-1-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-[4-(1,1-dioxo-1-6-isothiazolidin-2-yl)-phenyl]-methanone;

{(3SR,4RS)-3-(3,4-dichloro-phenyl)-4-[(3-fluoro-4-trifluoromethyl-benzyl)-methyl-amino]-pyrrolidin-1-yl}-(4-pyridin-2-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-pyridin-3-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-pyridin-4-yl-phenyl)-methanone;

{(3SR,4RS)-3-(3,4-dichloro-phenyl)-4-[(3-fluoro-4-trifluoromethyl-benzyl)-methyl-amino]-pyrrolidin-1-yl}-(4-[1,3,4]oxadiazol-2-yl-phenyl)-methanone;

N-(4-{(3SR,4RS)-3-(3,4-dichloro-phenyl)-4-[(3-fluoro-4-trifluoromethyl-benzyl)-methyl-amino]-pyrrolidine-1-carbonyl}-phenyl)-acetamide;

4-{(3SR,4RS)-3-(4-chloro-3-fluoro-phenyl)-4-[(3-fluoro-4-trifluoromethyl-benzyl)-methyl-amino]-pyrrolidine-1-carbonyl}-benzonitrile;

{(3SR,4RS)-3-(3,4-dichloro-phenyl)-4-[(3-fluoro-4-trifluoromethyl-benzyl)-methyl-amino]-pyrrolidin-1-yl}-(4-oxazol-5-yl-phenyl)-methanone; and 4-{(3SR,4RS)-3-(3,4-dichloro-phenyl)-4-[methyl-(4-trifluoromethyl-benzyl)-amino]-pyrrolidine-1-carbonyl}-benzonitrile.

Compounds of formula I, wherein $Ar^1$ is heteroaryl and $Ar^2$ is phenyl are further preferred.

Preferred specific compounds are the following:

benzo[1,3]dioxol-5-yl-{(3SR,4RS)-3-(3,4-dichloro-phenyl)-4-[(3-fluoro-4-trifluoromethyl-benzyl)-methyl-amino]-pyrrolidin-1-yl}-methanone;

{(3SR,4RS)-3-(3,4-dichloro-phenyl)-4-[(3-fluoro-4-trifluoromethyl-benzyl)-methyl-amino]-pyrrolidin-1-yl}-(6-methyl-pyridin-3-yl)-methanone;

5-{(3SR,4RS)-3-(3,4-dichloro-phenyl)-4-[(3-fluoro-4-trifluoromethyl-benzyl)-methyl-amino]-pyrrolidine-1-carbonyl}-pyridine-2-carbonitrile;

{(3SR,4RS)-3-(3,4-dichloro-phenyl)-4-[(3-fluoro-4-trifluoromethyl-benzyl)-methyl-amino]-pyrrolidin-1-yl}-(6-morpholin-4-yl-pyridin-3-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(6-fluoro-pyridin-3-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(6-methoxy-pyridin-3-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(6-pyrazol-1-yl-pyridin-3-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(2-methyl-pyridin-4-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(6-hydroxy-pyridin-3-yl)-methanone;

{(3SR,4RS)-3-(3,4-dichloro-phenyl)-4-[(3-fluoro-4-trifluoromethyl-benzyl)-methyl-amino]-pyrrolidin-1-yl}-[1,6]naphthyridin-2-yl-methanone;

{(3SR,4RS)-3-(3,4-dichloro-phenyl)-4-[(3-fluoro-4-trifluoromethyl-benzyl)-methyl-amino]-pyrrolidin-1-yl}-(2-methoxy-pyrimidin-5-yl)-methanone;

(3H-benzotriazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone;

(3H-benzoimidazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone;

4-(5-{(3SR,4RS)-3-(3,4-dichloro-phenyl)-4-[(3-fluoro-4-trifluoromethyl-benzyl)-methyl-amino]-pyrrolidine-1-carbonyl}-pyridin-2-yl)-piperazine-1-carboxylic acid tert-butyl ester; and {(3SR,4RS)-3-(3,4-dichloro-phenyl)-4-[(3-fluoro-4-trifluoromethyl-benzyl)-methyl-amino]-pyrrolidin-1-yl}-[6-(1,1-dioxo-1-6-thiomorpholin-4-yl)-pyridin-3-yl]-methanone.

Preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises a) coupling a compound of formula

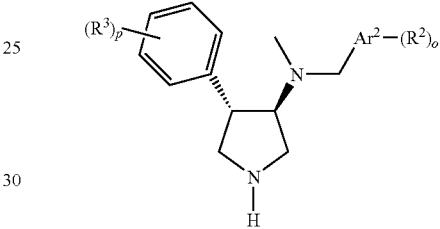

VIII with a suitable acid chloride or carboxylic acid of formula

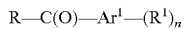

$R—C(O)—Ar^1—(R^1)_n$ wherein R is Cl or hydroxy,
to obtain a compound of formula

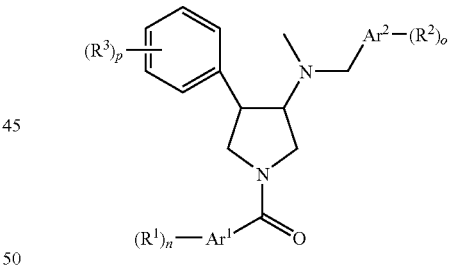

I wherein the substituents $R^1$, $R^2$, $R^3$, $Ar^1$, $Ar^2$ and the definitions o, n and p are described above, or b) alkylating a compound of formula

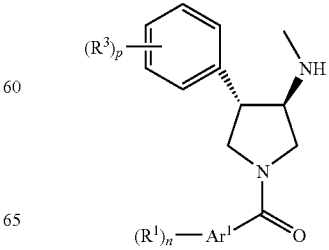

XII with a compound of formula

to obtain a compound of formula

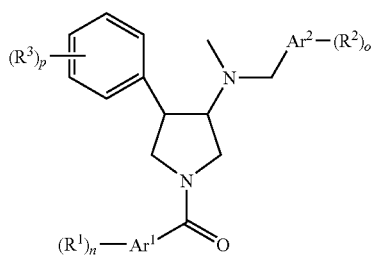

wherein the substituents R¹, R², R³, Ar¹, Ar² and the definitions o, n and p are described above, and, if desired, converting the compounds obtained into pharmaceutically acceptable acid addition salts.

The preparation of compounds of formula I is further described in more detail in schemes I-II and in examples 1-70.

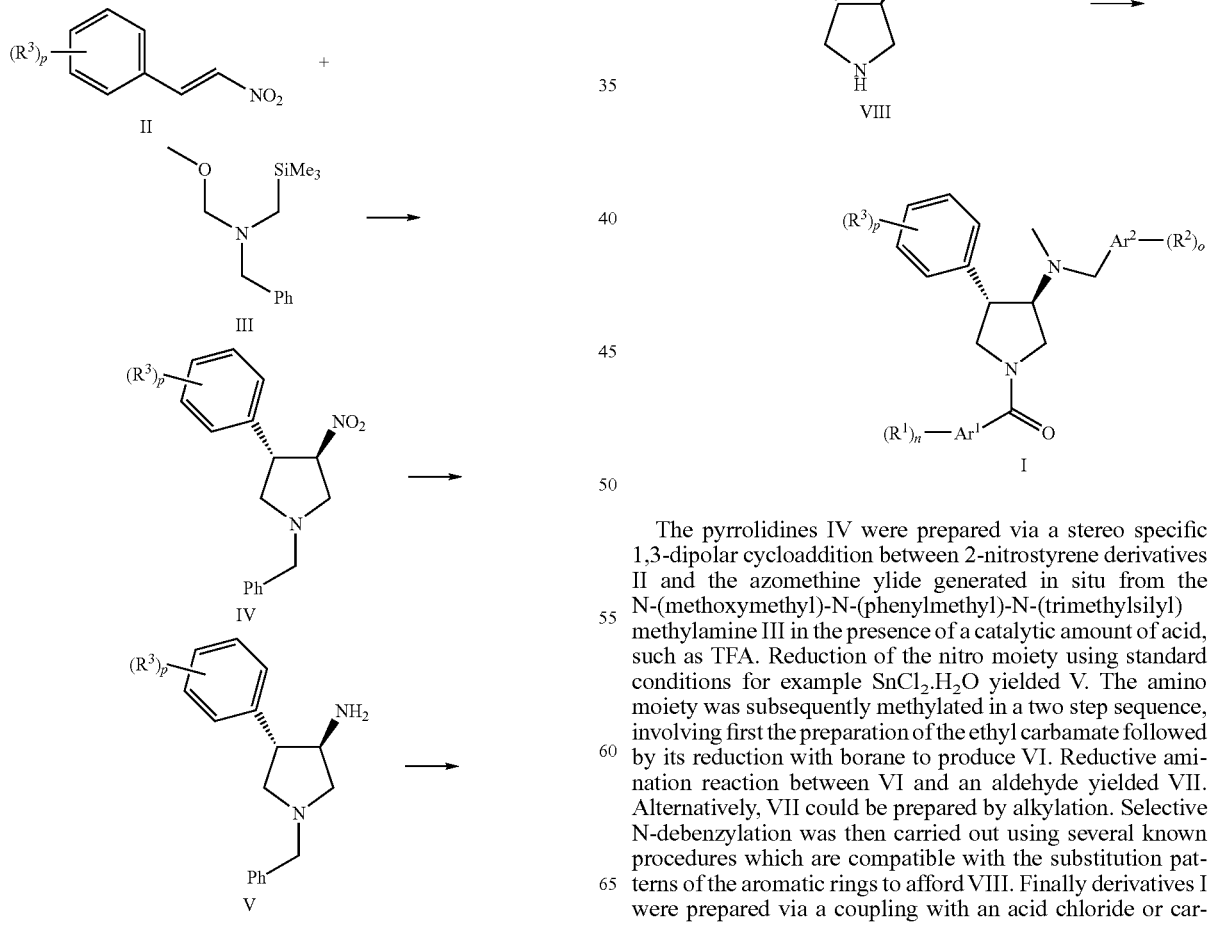

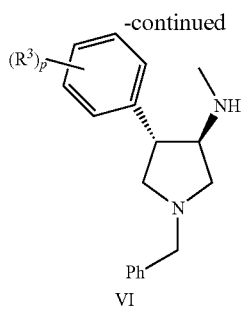

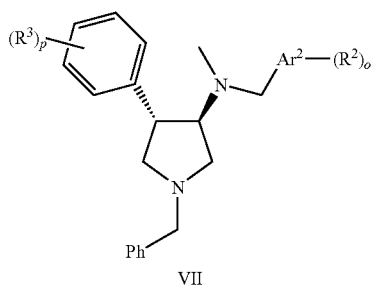

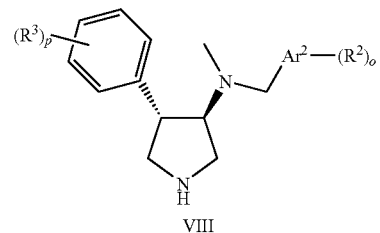

The pyrrolidines IV were prepared via a stereo specific 1,3-dipolar cycloaddition between 2-nitrostyrene derivatives II and the azomethine ylide generated in situ from the N-(methoxymethyl)-N-(phenylmethyl)-N-(trimethylsilyl) methylamine III in the presence of a catalytic amount of acid, such as TFA. Reduction of the nitro moiety using standard conditions for example $SnCl_2.H_2O$ yielded V. The amino moiety was subsequently methylated in a two step sequence, involving first the preparation of the ethyl carbamate followed by its reduction with borane to produce VI. Reductive amination reaction between VI and an aldehyde yielded VII. Alternatively, VII could be prepared by alkylation. Selective N-debenzylation was then carried out using several known procedures which are compatible with the substitution patterns of the aromatic rings to afford VIII. Finally derivatives I were prepared via a coupling with an acid chloride or carboxylic acid.

General scheme 2

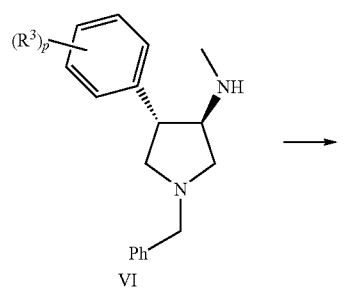
VI

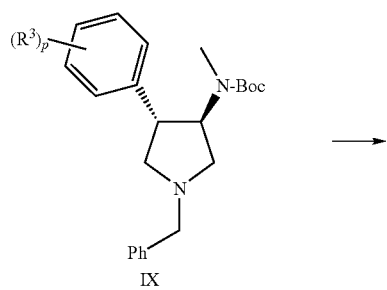
IX

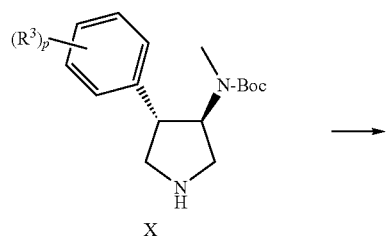
X

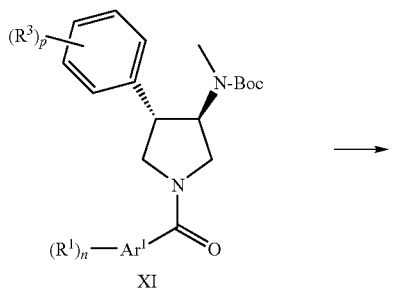
XI

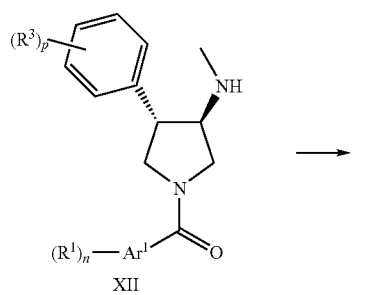
XII

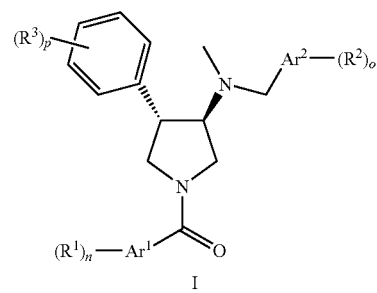
I

Alternatively, the pyrrolidine derivatives I, were also prepared via the route highlighted scheme 2. The secondary amine of the intermediate VI can be BOC-protected to afford IX. Selective N-debenzylation was then carried out using several known procedures which are compatible with the substitution patterns of the aromatic rings to afford X. Standard coupling reaction with an acid chloride or carboxylic acid gave XI, which could then undergo a deprotection with for instance TFA to give XII. The secondary amine was then alkylated via a standard reductive amination or via an alkylation with an alkyl-halide to afford the derivatives I.

Experimental Part

Abbreviations $CH_2Cl_2$=dichloromethane;
DMAP=dimethylaminopyridine;
HOBt=1-hydroxy-benzotriazol hydrat;
EDC=1-(3-dimethylaminopropyl)-3-ethylcarbodiimide hydrochloride;
$Et_3N$=triethylamine;
EtOAc=ethyl acetate;
H=hexane;
RT=room temperature;
General Procedure I (Amide Coupling)

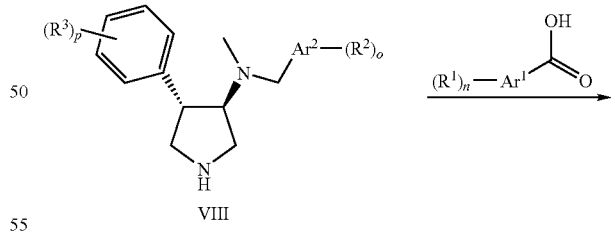
VIII → I

-continued

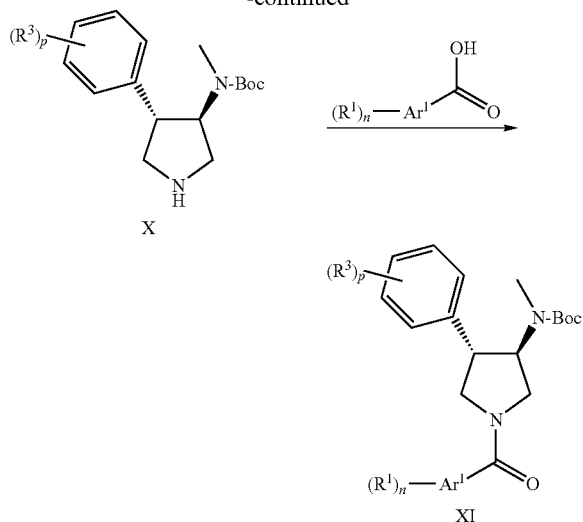

To a stirred solution of a carboxylic acid derivative (commercially available or known in the literature) (1 mmol) in 10 mL of CH$_2$Cl$_2$ was added (1.3 mmol) of EDC, (1.3 mmol) of HOBt and Et$_3$N (1.3 mmol). After one hour at RT, was added a pyrrolidine intermediate of general formula (VIII or X). The mixture was stirred at RT over night and then poured onto water and extracted with CH$_2$Cl$_2$. The combined organic phases were dried over Na$_2$SO$_4$ and concentrated under vacuo. Flash chromatography or preparative HPLC afforded the title compound.

General Procedure II

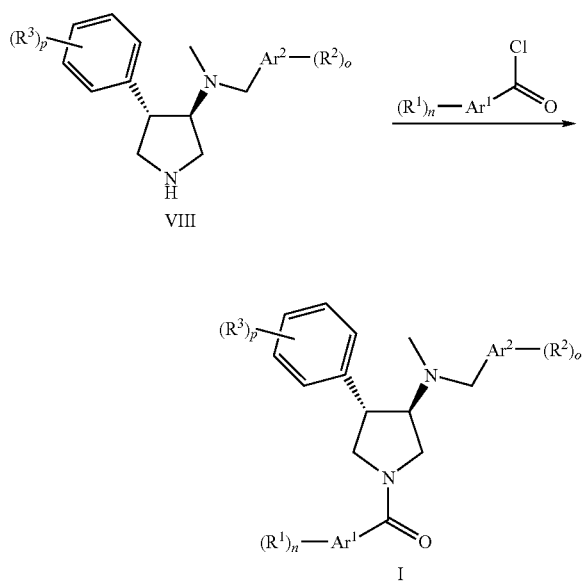

To a stirred solution of a pyrrolidine intermediate VIII (1 mmol) in CH$_2$Cl$_2$ (15 ml) at RT were added ethyl-diisopropyl-amine (2 mmol) and an acid chloride of formula ArCOCl (1.1 mmol). Stirring was continued until completion of the reaction. The reaction mixture was then concentrated under vacuo and purification by flash chromatography on SiO$_2$ or preparative HPLC.

General Procedure III (Reductive Amination)

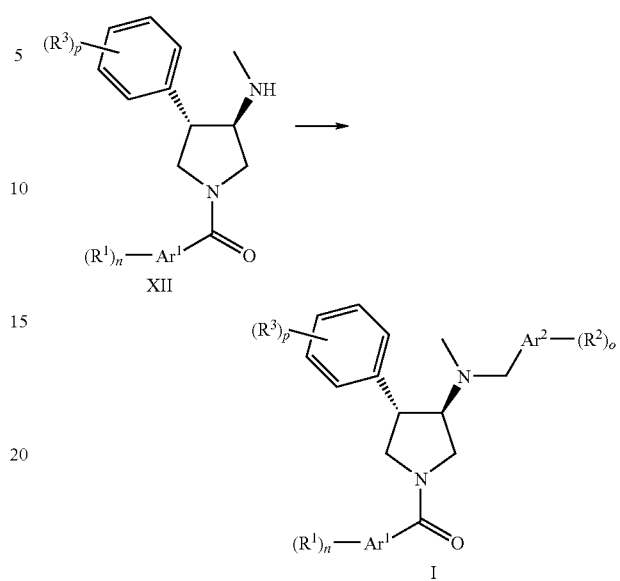

To a stirred solution of a pyrrolidine intermediate XII (1.00 mmol) in MeOH (6 ml) was added the aldehyde (1.20 mmol). Then a solution of NaBH$_3$CN (1.3 mol) in MeOH (1.5 ml) and AcOH (0.01 ml) were added. The reaction mixture was stirred overnight at RT, concentrated under vacuo, diluted with EtOAc, washed with H$_2$O. The organic phases were dried over Na$_2$SO$_4$ and the product purified by flash chromatography (SiO$_2$) or preparative HPLC to afford the desired compound.

As mentioned earlier, the compounds of formula I and their pharmaceutically usable addition salts possess valuable pharmacological properties. Compounds of the present invention are antagonists of neurokinin 3 (NK-3) receptors. The compounds were investigated in accordance with the tests given hereinafter.

Experimental Procedure

The compounds were investigated in accordance with the tests given hereinafter.

[$^3$H]SR142801 competition binding assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 μM SB222200 for both radioligands. The radioactivity on the filter was counted (5 min) on a Packard Top-count microplate scintillation counter with quenching correction after addition of 45 μl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

The $K_i$ values for some compounds with a hNK-3 receptor affinity<0.05 μM are shown in the following table 1.

TABLE 1

| Example | Data $K_i$ [μM] |
|---|---|
| 6 | 0.0209 |
| 9 | 0.0474 |
| 17 | 0.0383 |
| 18 | 0.042 |
| 19 | 0.0129 |
| 20 | 0.0417 |
| 22 | 0.0302 |
| 23 | 0.0066 |
| 24 | 0.0068 |
| 25 | 0.0152 |
| 26 | 0.0148 |
| 27 | 0.0057 |
| 28 | 0.0356 |
| 29 | 0.0084 |
| 30 | 0.0028 |
| 33 | 0.0111 |
| 38 | 0.009 |
| 40 | 0.0027 |
| 41 | 0.0107 |
| 42 | 0.0335 |
| 43 | 0.0051 |
| 44 | 0.0056 |
| 45 | 0.0025 |
| 47 | 0.0023 |
| 48 | 0.0478 |
| 51 | 0.0146 |
| 57 | 0.0223 |
| 59 | 0.0318 |
| 60 | 0.0173 |
| 61 | 0.0373 |
| 63 | 0.0247 |
| 64 | 0.002 |
| 66 | 0.0126 |
| 67 | 0.0045 |
| 68 | 0.0146 |

The present invention also provides pharmaceutical compositions containing compounds of the invention, for example compounds of formulae (I-a) to (I-e), or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

EXAMPLE A

Tablets of the following composition are manufactured in the usual manner:

|  | g/tablet |
|---|---|
| Active substance | 5 |
| Lactose | 5 |
| Corn starch | 5 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

Process for preparation of pyrrolidine intermediates of formula VIII

Pyrrolidine VIII-1

[(3RS,4SR)-4-(3,4-Dichloro-phenyl)-pyrrolidin-3-yl]-(3-fluoro-4-trifluoromethyl-benzyl)-methyl-amine

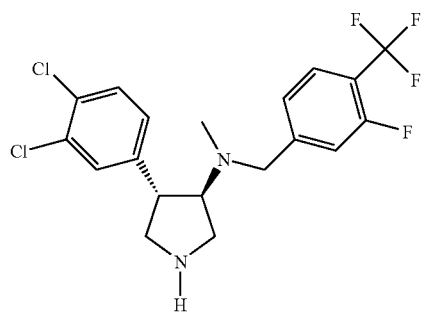

a) (3SR,4RS)-1-Benzyl-3-(3,4-dichloro-phenyl)-4-nitro-pyrrolidine

A solution of N-(methoxymethyl)-N-(phenylmethyl)-N-(trimethylsilyl)methylamine (1.96 g, 8.2 mmol) in $CH_2Cl_2$ (10 ml) was added drop wise, over a 30 minutes period, to a stirred solution of 1,2-dichloro-4-((E)-2-nitro-vinyl)-benzene (1.0 g, 4.58 mmol) and trifluoroacetic acid (52 mg, 4.45 mmol) in $CH_2Cl_2$ (5 ml) at 0° C. The ice bath was removed, and the solution was stirred at 25° C. for an additional 48 h. It was then concentrated and purification by flash chromatography ($SiO_2$, EtOAc/H 1:4) afforded 1.00 g (62%) of the title compound as a colorless oil. ES-MS m/e: 351.4 (M+H$^+$).

b) (3RS,4SR)-1-Benzyl-4-(3,4-dichloro-phenyl)-pyrrolidin-3-ylamine

To a stirred solution of (3SR,4RS)-1-benzyl-3-(3,4-dichloro-phenyl)-4-nitro-pyrrolidine (15.0 g, 0.0427 mol) in EtOAc (200 ml) was added portionwise $SnCl_2.2H_2O$ (43.36 g, 0.192 mol). The reaction mixture was then heated at reflux for 4 hours, cooled down to RT and a saturated aqueous solution of $NaHCO_3$ (500 ml) was added. The salts were filtered off and the product extracted with EtOAc. The organic phases were then dried over $Na_2SO_4$, and concentration under vacuum gave 9.30 g (75%) of the title compound as a light yellow oil. The product was then used in the next step without further purification. ES-MS m/e: 321.1 (M+H$^+$).

c) [(3RS,4SR)-1-Benzyl-4-(3,4-dichloro-phenyl)-pyrrolidin-3-yl]-methyl-amine To a solution of (3RS,4SR)-1-benzyl-4-(3,4-dichloro-phenyl)-pyrrolidin-3-ylamine (9.2 g, 0.028 mol) in THF (100 ml) was added a solution of $K_2CO_3$ (7.91 g, 0.057 mol) in $H_2O$ (35 ml). After 10 minutes, ethyl chloroformate (2.86 ml, 0.030 mol) was added and stirring was continued at RT for an additional 4 h. The intermediate carbamate was then extracted with $Et_2O$, dried over $Na_2SO_4$ and concentrated under vacuo to give viscous oil. The oil was taken up in THF (100 ml) and a solution of borane in THF (1M) was added (114.5 ml). The reaction mixture was then heated at 65° C. over night, cooled to RT and carefully quenched with conc. HCl (100 ml). The mixture was then heated at 80° C. for 2 h, cooled to RT, concentrated under vacuo, diluted with $Et_2O$ (100 ml) and neutralized with an aqueous solution of $NaHCO_3$. The organic phases were dried over $Na_2SO_4$ and the product purified by flash chromatography ($SiO_2$, $CH_2Cl_2$/MeOH 9:1) to afford 7.31 g (76%) of the title compound as a colorless oil. ES-MS m/e: 335.3 (M+H$^+$).

d) [(3RS,4SR)-1-Benzyl-4-(3,4-dichloro-phenyl)-pyrrolidin-3-yl]-(3-fluoro-4-trifluoromethyl-benzyl)-methyl-amine To a stirred solution of [(3RS,4SR)-1-Benzyl-4-(3,4-dichloro-phenyl)-pyrrolidin-3-yl]-methyl-amine (3.5 g, 0.010 mol) in MeOH (60 ml) was added 3-fluoro-4-trifluoromethyl-benzaldehyde (2.10 g, 0.0109 mol). Then a solution of $NaBH_3CN$ (0.79 g, 0.012 mol) in MeOH (15 ml) and AcOH (0.1 ml) were added. The reaction mixture was stirred overnight at RT, concentrated under vacuo, diluted with EtOAc, washed with $H_2O$. The organic phases were dried over $Na_2SO_4$ and the product purified by flash chromatography ($SiO_2$, EtOAc/Heptane 1:4) to afford 3.31 g (6 2%) of the title compound as a colorless oil.

e) [3RS,4SR)-4-(3,4-Dichloro-phenyl)-pyrrolidin-3-yl]-(3-fluoro-4-trifluoromethyl-benzyl)-methyl-amine To a stirred solution of [(3RS,4SR)-1-benzyl-4-(3,4-dichloro-phenyl)-pyrrolidin-3-yl]-(3-fluoro-4trifluoromethyl-benzyl)-methyl-amine (3.30 g, 6.45 mmol) in $CH_3CN$ (45 ml) at RT, was added 2,2,2-trichloroethyl chloroformate (1.30 ml, 9.67 mmol). The reaction mixture was stirred at RT for 3 hours, concentrated under vacuo. The residue was dissolved in AcOH (10 ml) and zinc dust (1.0 g) was added portion wise over 3 hours. The solvent was evaporated, the residue diluted in EtOAc and the organic phase was washed with an aqueous solution of NaHCO$_3$. The organic phase was dried over Na$_2$SO$_4$, concentrated under vacuo to afford 1.43 g (53%) of the tile compound as a colorless oil. ES-MS m/e: 421.0 (M+H$^+$).

Pyrrolidine VIII-2

[(3RS,4SR)-4-(3,4-Dichloro-phenyl)-pyrrolidin-3-yl]-methyl-(4-trifluoromethyl-benzyl)-amine

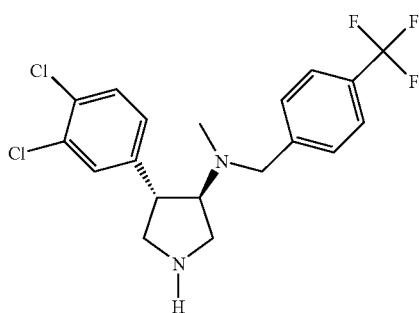

a)[(3RS,4SR)-1-Benzyl-4-(3,4-dichloro-phenyl)-pyrrolidin-3-yl]-methyl-(4-trifluoromethyl-benzyl)-amine To a stirred solution of [(3RS,4SR)-1-benzyl-4-(3,4-dichloro-phenyl)-pyrrolidin-3-yl]-methyl-amine (0.35 g, 1.04 mmol) in THF (6 ml) was added 1-bromomethyl-4-trifluoromethyl-benzene (0.27 g, 1.15 mmol) and Et$_3$N (0.148 ml, 1.45 mmol). The reaction mixture was stirred overnight at RT and concentrated under vacuo. The product purified by flash chromatography (SiO$_2$, EtOAc/Heptane 1:4) to afford 130 mg (29%) of the title compound as a colorless oil. ES-MS m/e: 492.9 (M+H$^+$).

b)[(3RS,4SR)-4-(3A-Dichloro-phenyl)-pyrrolidin-3-yl]-methyl-(4-trifluoromethyl-benzyl)-amine To a stirred solution of [(3RS,4SR)-1-benzyl-4-(3,4-dichloro-phenyl)-pyrrolidin-3-yl]-methyl-(4-trifluoromethyl-benzyl)-amine (160 mg, 0.32 mmol) in CH$_3$CN (5 ml) at RT, was added 2,2,2-trichloroethyl chloroformate (0.070 ml, 0.48 mmol). The reaction mixture was stirred at RT for 3 hours, concentrated under vacuo. The residue was dissolved in AcOH (3 ml) and zinc dust (80 mg) was added portion wise over 1 hours. The solvent was evaporated, the residue diluted in EtOAc and the organic phase was washed with an aqueous solution of NaHCO$_3$. The organic phase was dried over Na$_2$SO$_4$ and concentrated under vacuo. The product was purified by column chromatography (CH$_2$Cl$_2$/MeOH: 9/1) to afford 85 mg (65%) of the tile compound as a colorless oil. ES-MS m/e: 403.4 (M+H$^+$).

Pyrrolidine VIII-3

[(3RS,4SR)-4-(4-Chloro-3-fluoro-phenyl)-pyrrolidin-3-yl]-(3-fluoro-4-trifluoromethyl-benzyl)-methyl-amine

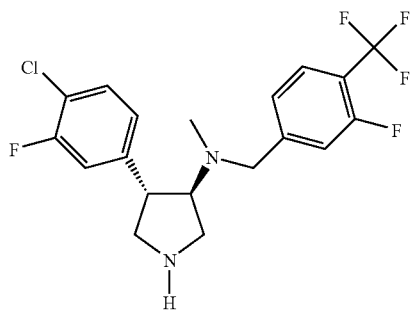

a) (3SR,4RS)-1-Benzyl-3-(4-chloro-3-fluoro-phenyl)-4-nitro-pyrrolidine

A solution of N-(methoxymethyl)-N-(phenylmethyl)-N-(trimethylsilyl)methylamine (1.00 g, 4.2 mmol) in CH$_2$Cl$_2$ (5 ml) was added drop wise, over a 30 minutes period, to a stirred solution of 1-chloro-2-fluoro-4-((E)-2-nitro-vinyl)-benzene (0.68 g, 3.37 mmol) and trifluoroacetic acid (30 ul) in CH$_2$Cl$_2$ (5 ml) at 0° C. The ice bath was removed, and the solution was stirred at 25° C. for an additional 48 h. It was then concentrated and purification by flash chromatography (SiO$_2$, EtOAc/H 1:4) afforded 0.78 g (55%) of the title compound as a colorless oil. ES-MS m/e: 335.2 (M+H$^+$).

b) (3RS,4SR)-1-Benzyl-4-(4-chloro-3-fluoro-phenyl)-pyrrolidin-3-ylamine

To a stirred solution of (3SR,4RS)-1-benzyl-3-(4-chloro-3-fluoro-phenyl)-4-nitro-pyrrolidine (0.78 g, 2.33 mmol) in EtOAc (15 ml) was added portion wise SnCl$_2$.2H$_2$O (2.63 g, 11.6 mmol). The reaction mixture was then heated at reflux for 4 hours, cooled down to RT and a saturated aqueous solution of NaHCO$_3$ (500 ml) was added. The salts were filtered off and the product extracted with EtOAc. The organic phases were then dried over Na$_2$SO$_4$, and concentration under vacuum. A column chromatography (CH$_2$Cl$_2$/MeOH 95/5) gave 0.46 g (65%) of the title compound as a light brown oil. ES-MS m/e: 305.1 (M+H$^+$).

c) [(3RS,4SR)-1-Benzyl-4-(4-chloro-3-fluoro-phenyl)-pyrrolidin-3-yl]-methyl-amine To a solution of (3RS,4SR)-1-benzyl-4-(4-chloro-3-fluoro-phenyl)-pyrrolidin-3-ylamine (0.46 g, 1.51 mmol) in THF (5 ml) was added a solution of K$_2$CO$_3$ (0.419 g, 3.0 mmol) in H$_2$O (2 ml). After 10 minutes, ethyl chloroformate (0.3 ml, 3.0 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (10 ml) and a solution of borane in THF (1M) was added (6.0 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et₂O (10 ml) and neutralized with an aqueous solution of NaHCO₃. The organic phases were dried over Na₂SO₄ and the product purified by flash chromatography (SiO₂, CH₂Cl₂/MeOH 9:1) to afford 0.34 g (70%) of the title compound as a colorless oil. ES-MS m/e: 319.1 (M+H⁺).

d) [(3RS,4SR)-1-Benzyl-4-(4-chloro-3-fluoro-phenyl)-pyrrolidin-3-yl]-(3-fluoro-4-trifluoromethyl-benzyl)-methyl-amine To a stirred solution of [(3RS,4SR)-1-benzyl-4-(4-chloro-3-fluoro-phenyl)-pyrrolidin-3-yl]-methyl-amine (340 mg, 1.06 mmol) in MeOH (6 ml) was added 3-fluoro-4-trifluoromethyl-benzaldehyde (230 mg, 1.20 mmol). Then a solution of NaBH₃CN (85 mg, 1.3 mol) in MeOH (1.5 ml) and AcOH (0.01 ml) were added. The reaction mixture was stirred overnight at RT, concentrated under vacuo, diluted with EtOAc, washed with H₂O. The organic phases were dried over Na₂SO₄ and the product purified by flash chromatography (SiO₂, EtOAc/Heptane 1:4) to afford 145 mg (28%) of the title compound as a colorless oil.

e) [(3RS,4SR)-4-(4-Chloro-3-fluoro-phenyl)-pyrrolidin-3-yl]-(3-fluoro-4-trifluoromethyl-benzyl)-methyl-amine To a stirred solution of [(3RS,4SR)-1-benzyl-4-(4-chloro-3-fluoro-phenyl)-pyrrolidin-3-yl]-(3-fluoro-4-trifluoromethyl-benzyl)-methyl-amine (145 mg, 0.29 mmol) in CH₃CN (2 ml) at RT, was added 2,2,2-trichloroethyl chloroformate (0.06 ml, 0.44 mmol). The reaction mixture was stirred at RT for 3 hours, concentrated under vacuo. The residue was dissolved in AcOH (3 ml) and zinc dust (60 mg) was added portion wise over 3 hours. The solvent was evaporated, the residue diluted in EtOAc and the organic phase was washed with an aqueous solution of NaHCO₃. The organic phase was dried over Na₂SO₄, concentrated under vacuo to afford 80 mg (67%) of the tile compound as a colorless oil. ES-MS m/e: 405.3 (M+H⁺).

Pyrrolidine VIII-4

[(3RS,4SR)-4-(3-Chloro-phenyl)-pyrrolidin-3-yl]-(3-fluoro-4-trifluoromethyl-benzyl)-methyl-amine

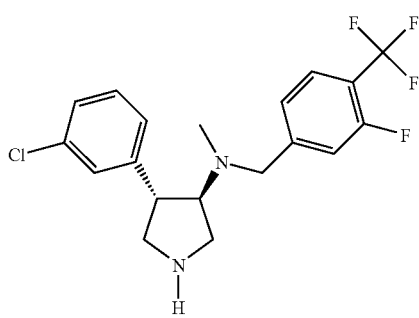

a) (3SR,4RS)-1-Benzyl-3-(3-chloro-phenyl)-4-nitro-pyrrolidine

A solution of N-(methoxymethyl)-N-(phenylmethyl)-N-(trimethylsilyl)methylamine (9.69 g, 41 mmol) in CH₂Cl₂ (40 ml) was added drop wise, over a 30 minutes period, to a stirred solution of 1-chloro-3-((E)-2-nitro-vinyl)-benzene (0.68 g, 3.37 mmol) and trifluoroacetic acid (0.21 ml) in CH₂Cl₂ (40 ml) at 0° C. The ice bath was removed, and the solution was stirred at 25° C. for an additional 48 h. It was then concentrated and purification by flash chromatography (SiO₂, EtOAc/H 1:4) afforded 6.30 g (73%) of the title compound as a colorless oil. ES-MS m/e: 317.1 (M+H⁺).

b) (3RS,4SR)-1-Benzyl-4-(3-chloro-phenyl)-pyrrolidin-3-ylamine

To a stirred solution of (3SR,4RS)-1-benzyl-3-(3-chloro-phenyl)-4-nitro-pyrrolidine (6.30 g, 19.8 mmol) in EtOAc (150 ml) was added portion wise SnCl₂.2H₂O (22.43 g, 99 mmol). The reaction mixture was then heated at reflux for 4 hours, cooled down to RT and a saturated aqueous solution of NaHCO₃ (500 ml) was added. The salts were filtered off and the product extracted with EtOAc. The organic phases were then dried over Na₂SO₄, and concentration under vacuum. A column chromatography (CH₂Cl₂/MeOH 95/5) gave 4.47 g (78%) of the title compound as a light yellow oil. ES-MS m/e: 287.0 (M+H⁺).

c) [(3RS,4SR)-1-Benzyl-4-(3-chloro-phenyl)-pyrrolidin-3-yl]-methyl-amine

To a solution of (3RS,4SR)-1-benzyl-4-(3-chloro-phenyl)-pyrrolidin-3-ylamine (4.47 g, 16.0 mmol) in THF (50 ml) was added a solution of K₂CO₃ (4.31 g, 31 mmol) in H₂O (35 ml). After 10 minutes, ethyl chloroformate (2.97 ml, 31 mmol) was added and stirring was continued at RT for an additional 4 h. The intermediate carbamate was then extracted with Et₂O, dried over Na₂SO₄ and concentrated under vacuo to give viscous oil. The oil was taken up in THF (10 ml) and a solution of borane in THF (1M) was added (62 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et₂O (50 ml) and neutralized with an aqueous solution of NaHCO₃. The organic phases were dried over Na₂SO₄ and the product purified by flash chromatography (SiO₂, CH₂Cl₂/MeOH 9:1) to afford 2.68 g (57%) of the title compound as a colorless oil. ES-MS m/e: 301.2 (M+H⁺).

d) [(3RS,4SR)-1-Benzyl-4-(3-chloro-phenyl)-pyrrolidin-3-yl]-(3-fluoro-4-trifluoromethyl-benzyl)-methyl-amine To a stirred solution of [(3RS,4SR)-1-benzyl-4-(3-chloro-phenyl)-pyrrolidin-3-yl]-methyl-amine (2.20 g, 7.31 mmol) in THF (70 ml) was added 4-bromomethyl-2-fluoro-1-trifluoromethyl-benzene (2.25 g, 8.75 mmol) and Et₃N (1.21 ml, 8.75 mmol). The reaction mixture was stirred overnight at 40° C., concentrated under vacuo, diluted with EtOAc, washed with H₂O. The organic phase was dried over Na₂SO₄ and the product purified by flash chromatography (SiO₂, EtOAc/Heptane 1:3) to afford 2.0 g (57%) of the title compound as a colorless oil.

e) [(3RS,4SR)-4-(3-Chloro-phenyl)-pyrrolidin-3-yl]-(3-fluoro-4-trifluoromethyl-benzyl)-methyl-amine To a stirred solution of [(3RS,4SR)-1-benzyl-4-(3-chloro-phenyl)-pyrrolidin-3-yl]-(3-fluoro-4-trifluoromethyl-benzyl)-methyl-amine (2.0 g, 4.19 mmol) in $CH_3CN$ (28 ml) at RT, was added 2,2,2-trichloroethyl chloroformate (0.85 ml, 6.3 mmol). The reaction mixture was stirred at RT for 3 hours, concentrated under vacuo. The residue was dissolved in AcOH (25 ml) and zinc dust (800 mg) was added portion wise over 3 hours. The solvent was evaporated, the residue diluted in EtOAc and the organic phase was washed with an aqueous solution of $NaHCO_3$. The organic phase was dried over $Na_2SO_4$, concentrated under vacuo to afford 0.90 g (44%) of the tile compound as a light brown oil. ES-MS m/e: 387.2 $(M+H^+)$.

Pyrrolidine VIII-5

[(3RS,4SR)-4-(3-Chloro-phenyl)-pyrrolidin-3-yl]-methyl-(4-trifluoromethyl-benzyl)-amine

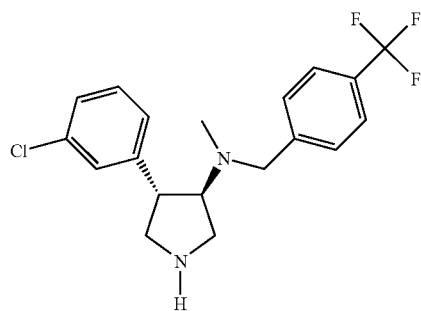

a) [(3RS,4SR)-1-Benzyl-4-(3-chloro-phenyl)-pyrrolidin-3-yl]-methyl-(4-trifluoromethyl-benzyl)-amine To a stirred solution of [(3RS,4SR)-1-benzyl-4-(3-chloro-phenyl)-pyrrolidin-3-yl]-methyl-amine (0.46 g, 1.59 mmol) in THF (15 ml) was added 1-bromomethyl-4-trifluoromethyl-benzene (0.44 g, 1.86 mmol) and $Et_3N$ (0.155 ml, 1.59 mmol). The reaction mixture was stirred overnight at RT and concentrated under vacuo. The product purified by flash chromatography ($SiO_2$, EtOAc/Heptane 1:4) to afford 500 mg (71%) of the title compound as a colorless oil. ES-MS m/e: 459.3 $(M+H^+)$.

b) [(3RS,4SR)-4-(3-chloro-phenyl)-pyrrolidin-3-yl]-methyl-(4-trifluoromethyl-benzyl)-amine To a stirred solution of [(3RS,4SR)-1-benzyl-4-(3-chloro-phenyl)-pyrrolidin-3-yl]-methyl-(4-trifluoromethyl-benzyl)-amine (500 mg, 1.09 mmol) in $CH_3CN$ (7 ml) at RT, was added 2,2,2-trichloroethyl chloroformate (0.22 ml, 1.63 mmol). The reaction mixture was stirred at RT for 3 hours, concentrated under vacuo. The residue was dissolved in AcOH (5 ml) and zinc dust (200 mg) was added portion wise over 1 hours. The solvent was evaporated, the residue diluted in EtOAc and the organic phase was washed with an aqueous solution of $NaHCO_3$. The organic phase was dried over $Na_2SO_4$ and concentrated under vacuo. The product was purified by column chromatography ($CH_2Cl_2$/MeOH: 9/1) to afford 305 mg (76%) of the tile compound as a colorless oil. ES-MS m/e: 369.2 $(M+H^+)$.

Process for preparation of pyrrolidine intermediates of formula XII

Pyrrolidine XII-1

[(3SR,4RS)-3-(4-Chloro-phenyl)-4-methylamino-pyrrolidin-1-yl]-phenyl-methanone

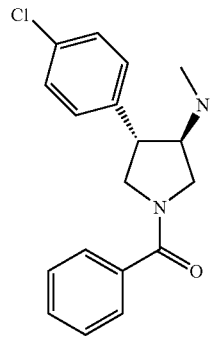

a) (3SR,4SR)-1-Benzyl-3-(4-chloro-phenyl)-4-nitro-pyrrolidine

A solution of N-(methoxymethyl)-N-(phenylmethyl)-N-(trimethylsilyl)methylamine (6.70 g, 28.2 mmol) in $CH_2Cl_2$ (100 ml) was added drop wise, over a 30 minutes period, to a stirred solution of 1-chloro-4-((E)-2-nitro-vinyl)-benzene (4.97 g, 27.1 mmol) and trifluoroacetic acid (0.31 g, 2.7 mmol) in $CH_2Cl_2$ (150 ml) at 0° C. The ice bath was removed, and the solution was stirred at 25° C. for an additional 48 h. It was then concentrated and purification by flash chromatography ($SiO_2$, EtOAc/H 1:4) afforded 6.75 g (79%) of the title compound as a colorless oil.

b) (3RS,4SR)-1-Benzyl-4-(4-chloro-phenyl)-pyrrolidin-3-ylamine

Titanium (IV) chloride (0.36 g, 1.89 mmol) was added drop wise to a suspension of zinc powder (0.25 g, 3.78 mmol) in THF (3 ml). This solution was heated at 68° C. for one hour, then cooled to RT before (3SR,4RS)-1-benzyl-3-(4-chloro-phenyl)-4-nitro-pyrrolidine (0.20 g, 0.63 mmol) in THF (2 ml) was added. The reaction mixture was then stirred at reflux over night. The reaction was cooled to RT, diluted with 300 ml of $Et_2O$, washed with an aqueous solution of $NaHCO_3$ and the organic phases were dried over $Na_2SO_4$. Flash chromatography ($SiO_2$, $CH_2Cl_2$/MeOH, 9:1) yielded 0.10 g (57%) of (3RS,4SR)-1-benzyl-4-(4-chloro-phenyl)-pyrrolidin-3-ylamine as a light yellow oil.

c) [(3RS,4SR)-1-Benzyl-4-(4-chloro-phenyl)-pyrrolidin-3-yl]-methyl-amine

To a solution of (3RS,4SR)-1-benzyl-4-(4-chloro-phenyl)-pyrrolidin-3-ylamine (1.86 g, 6.51 mmol) in THF (20 ml) was added a solution of K$_2$CO$_3$ (1.80 g, 13.02 mmol) in H$_2$O (15 ml). After 10 minutes, ethyl chloroformate (0.68 ml, 7.16 mmol) was added and stirring was continued at RT for an additional 4 h. The intermediate carbamate was then extracted with Et$_2$O, dried over Na$_2$SO$_4$ and concentrated under vacuo to give viscous oil. The oil was taken up in THF (20 ml) and a solution of borane in THF (1M) was added (26 ml). The reaction mixture was then heated at 65° C. over night, cooled to RT and carefully quenched with conc. HCl (5 ml). The mixture was then heated at 80° C. for 2 h, cooled to RT, concentrated under vacuo, diluted with Et$_2$O (100 ml) and neutralized with an aqueous solution of NaHCO$_3$. The organic phases were dried over Na$_2$SO$_4$ and the product purified by flash chromatography (SiO$_2$, CH$_2$Cl$_2$/MeOH 9:1) to afford 1.51 g (77%) of rac-[(3S,4R)-1-benzyl-4-(4-chloro-phenyl)-pyrrolidin-3-yl]-methyl-amine as a colorless oil.

d)[(3RS,4SR)-1-Benzyl-4-(4-chloro-phenyl)-pyrrolidin-3-yl]-methyl-carbamic acid tert-butyl ester To a stirred solution of [(3RS,4SR)-1-benzyl-4-(4-chloro-phenyl)-pyrrolidin-3-yl]-methyl-amine (2.75 g, 9.14 mmol) in CH$_2$Cl$_2$ (25 ml) was added Et$_3$N (2.50 ml, 18.2 mmol), DMAP (112 mg, 0.91 mmol) and (Boc)$_2$O (2.39 g, 10.95 mmol). After one hour at RT, the organic phase was washed with H$_2$O, then dried over Na$_2$SO$_4$. Column chromatography (Heptane/EtOAc:3/1) afforded 2.60 g (71%) of the title compound as a yellow oil. ES-MS m/e: 401.3 (M+H$^+$).

e) [(3RS,4SR)-4-(4-Chloro-phenyl)-pyrrolidin-3-yl]-methyl-carbamic acid tert-butyl ester To a stirred solution of [(3RS,4SR)-1-benzyl-4-(4-chloro-phenyl)-pyrrolidin-3-yl]-methyl-carbamic acid tert-butyl ester (1.30 g, 3.20 mmol) in toluene (30 ml) at RT, was added 1-chloroethyl chloroformate (0.53 ml, 4.80 mmol). The reaction mixture was stirred at 90° C. overnight and concentrated under vacuo. The residue was dissolved in MeOH (30 ml) and the reaction mixture was heated at 80° C. for 2 hours. The solvent was evaporated and the crude product was directly used in the next step without further purification.

e) [(3 RS,4SR)-1-Benzoyl-4-(4-chloro-phenyl)-pyrrolidin-3-yl]-methyl-carb amic acid tert-butyl ester Using the standard amide coupling (general procedure I), 82 mg of the title compound was produce from [(3RS,4SR)-4-(4-chloro-phenyl)-pyrrolidin-3-yl]-methyl-carbamic acid tert-butyl ester and benzoic acid as a white foam. ES-MS m/e: 415.3 (M+H$^+$).

f) [(3SR,4RS)-3-(4-Chloro-phenyl)-4-methylamino-pyrrolidin-1-yl]-phenyl-methanone To a stirred solution of [(3RS,4SR)-1-benzoyl-4-(4-chloro-phenyl)-pyrrolidin-3-yl]-methyl-carbamic acid tert-butyl ester (80 mg, 0.19 mmol) in CH$_2$Cl$_2$ (1 ml) was added TFA (0.2 ml). The reaction mixture was stirred at RT for 2 hours, aqueous NaHCO$_3$ was added until pH=8 and the product was extracted with CH$_2$Cl$_2$. The combined organic phase were dried over Na$_2$SO$_4$. Concentration under vacuo gave 64 mg (95%) of the title product as a colorless oil. ES-MS m/e: 315.1 (M+H$^+$).

Pyrrolidine XII-2

[(3SR,4RS)-3-(4-Chloro-phenyl)-4-methylamino-pyrrolidin-1-yl]-(3,4,5-trimethoxy-phenyl)-methanone

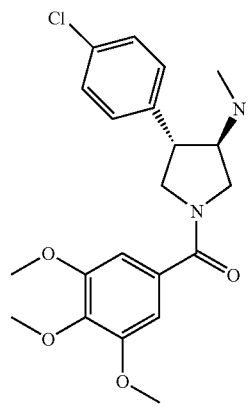

a) [(3RS,4SR)-4-(4-Chloro-phenyl)-1-(3,4,5-trimethoxy-benzoyl)-pyrrolidin-3-yl]-methyl-carbamic acid tert-butyl ester Using the standard amide coupling (general procedure I), 75 mg of the title compound was produce from [(3RS,4SR)-4-(4-chloro-phenyl)-pyrrolidin-3-yl]-methyl-carbamic acid tert-butyl ester and 3,4,5-trimethoxy-benzoic acid as a white foam. ES-MS m/e: 505.3 (M+H$^+$).

b) [(3SR,4RS)-3-(4-Chloro-phenyl)-4-methylamino-pyrrolidin-1-yl]-(3,4,5-trimethoxy-phenyl-methanone To a stirred solution of [(3RS,4SR)-4-(4-chloro-phenyl)-1-(3,4,5-trimethoxy-benzoyl)-pyrrolidin-3-yl]-methyl-carbamic acid tert-butyl ester (75 mg, 0.15 mmol) in CH$_2$Cl$_2$ (1 ml) was added TFA (0.2 ml). The reaction mixture was stirred at RT for 2 hours, aqueous NaHCO$_3$ was added until pH=8 and the product was extracted with CH$_2$Cl$_2$. The combined organic phase were dried over Na$_2$SO$_4$. Concentration under vacuo gave 62 mg (96%) of the title product as a colorless oil. ES-MS m/e: 405.4 (M+H$^+$).

Pyrrolidine XII-3

4-[(3SR,4RS)-3-(3,4-Dichloro-phenyl)-4-methylamino-pyrrolidine-1-carbonyl]-benzonitrile

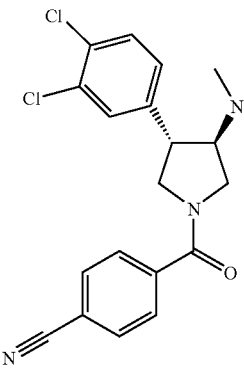

a) [(3RS,4SR)-1-Benzyl-4-(3,4-dichloro-phenyl)-pyrrolidin-3-yl]-methyl-carbamic acid tert-butyl ester To a stirred solution of [(3RS,4SR)-1-benzyl-4-(3,4-dichloro-phenyl)-pyrrolidin-3-yl]-methyl-amine (1.00 g, 2.98 mmol) in CH₂Cl₂ (10 ml) was added Et₃N (0.83 ml, 5.96 mmol), DMAP (73 mg, 0.59 mmol) and (Boc)₂O (1.43 g, 6.55 mmol). After one hour at RT, the organic phase was washed with H₂O, then dried over Na₂SO₄. Column chromatography (Heptane/EtOAc:3/1) afforded 0.93 g (71%) of the title compound as a yellow oil. ES-MS m/e: 435.3 (M+H⁺).

b) [(3R,4S)-4-(3,4-Dichloro-phenyl)-pyrrolidin-3-yl]-methyl-carbamic acid tert-butyl ester To a stirred solution of [(3RS,4SR)-1-benzyl-4-(3,4-dichloro-phenyl)-pyrrolidin-3-yl]-methyl-carbamic acid tert-butyl ester (928 mg, 2.13 mmol) in CH₃CN (10 ml) at RT, was added 2,2,2-trichloroethyl chloroformate (0.45 ml, 2.13 mmol). The reaction mixture was stirred at RT for 3 hours, concentrated under vacuo. The residue was dissolved in AcOH (5 ml) and zinc dust (400 mg) was added portion wise over 1 hours. The solvent was evaporated, the residue diluted in EtOAc and the organic phase was washed with an aqueous solution of NaHCO₃. The organic phase was dried over Na₂SO₄ and concentrated under vacuo to afford 415 mg (98%) of the tile compound as a light yellow oil. ES-MS m/e: 345.2 (M+H⁺).

c) [(3RS,4SR)-1-(4-Cyano-benzoyl)-4-(3,4-dichloro-phenyl)-pyrrolidin-3-yl]-methyl-carbamic acid tert-butyl ester Using the standard amide coupling (general procedure I), 414 mg of the title compound was produce from [(3RS,4S)-4-(3,4-dichloro-phenyl)-pyrrolidin-3-yl]-methyl-carbamic acid tert-butyl ester and 4-cyano-benzoic acid as a white powder. ES-MS m/e: 474.0 (M+H⁺).

d) 4-[(3SR,4RS)-3-(3,4-Dichloro-phenyl)-4-methylamino-pyrrolidine-1-carbonyl]-benzonitrile To a stirred solution of [(3RS,4SR)-1-(4-cyano-benzoyl)-4-(3,4-dichloro-phenyl)-pyrrolidin-3-yl]-methyl-carbamic acid tert-butyl ester (414 mg, 0.87 mmol) in CH₂Cl₂ (8 ml) was added TFA (2 ml). The reaction mixture was stirred at RT for 2 hours, aqueous NaHCO₃ was added until pH=8 and the product was extracted with CH₂Cl₂. The combined organic phase were dried over Na₂SO₄. Concentration under vacuo gave 302 mg (92%) of the title product as a colorless oil. ES-MS m/e: 374.1 (M+H⁺).

EXAMPLE 1

{(3SR,4RS)-3-(4-Chloro-phenyl)-4-[(3,4-dichloro-benzyl)-methyl-amino]-pyrrolidin-1-yl}-phenyl-methanone

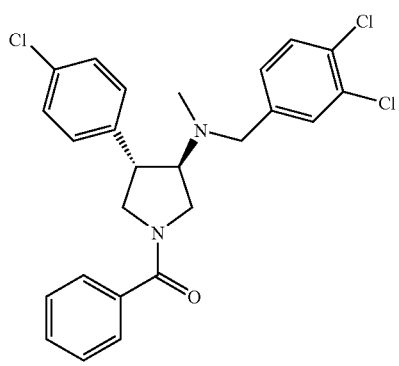

Reductive amination according to general procedure III:

Pyrrolidine intermediate: [(3SR,4RS)-3-(4-Chloro-phenyl)-4-methylamino-pyrrolidin-1-yl]-phenyl-methanone (XII-1), Aldehyde: 3,4-Dichloro-benzaldehyde (commercially available), ES-MS m/e: 475.1 (M+H⁺).

EXAMPLE 2

{(3SR,4RS)-3-(4-Chloro-phenyl)-4-[(3-fluoro-4-trifluoromethyl-benzyl)-methyl-amino]-pyrrolidin-1-yl}-phenyl-methanone

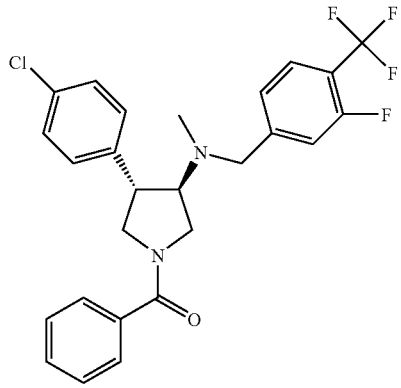

Reductive amination according to general procedure III:

Pyrrolidine intermediate: [(3SR,4RS)-3-(4-Chloro-phenyl)-4-methylamino-pyrrolidin-1-yl]-phenyl-methanone (XII-1), Aldehyde: 3-Fluoro-4-trifluoromethyl-benzaldehyde (commercially available),
ES-MS m/e: 491.3 (M+H⁺).

EXAMPLE 3

{(3SR,4RS)-3-(4-Chloro-phenyl)-4-[(3,4-dichloro-benzyl)-methyl-amino]-pyrrolidin-1-yl}-(3,4,5-trimethoxy-phenyl)-methanone

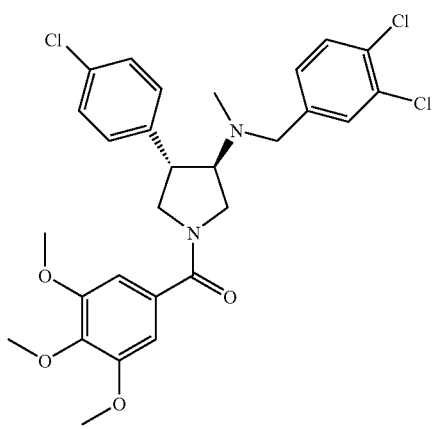

Reductive amination according to general procedure III:
Pyrrolidine intermediate: [(3SR,4RS)-3-(4-Chloro-phenyl)-4-methylamino-pyrrolidin-1-yl]-(3,4,5-trimethoxy-phenyl)-methanone (XII-2),
Aldehyde: 3,4-Dichloro-benzaldehyde (commercially available),
ES-MS m/e: 563.2 (M+H⁺).

EXAMPLE 4

{(3SR,4RS)-3-(4-Chloro-phenyl)-4-[(3-fluoro-4-trifluoromethyl-benzyl)-methyl-amino]-pyrrolidin-1-yl}-(3,4,5-trimethoxy-phenyl)-methanone

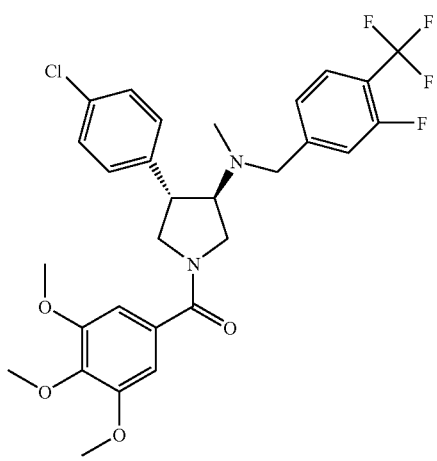

Reductive amination according to general procedure III:
Pyrrolidine intermediate: [(3SR,4RS)-3-(4-Chloro-phenyl)-4-methylamino-pyrrolidin-1-yl]-(3,4,5-trimethoxy-phenyl)-methanone (XII-2), Aldehyde: 3-Fluoro-4-trifluoromethyl-benzaldehyde (commercially available),
ES-MS m/e: 581.2 (M+H⁺).

EXAMPLE 5

{(3SR,4RS)-3-(3,4-Dichloro-phenyl)-4-[(3-fluoro-4-trifluoromethyl-benzyl)-methyl-amino]-pyrrolidin-1-yl}-phenyl-methanone

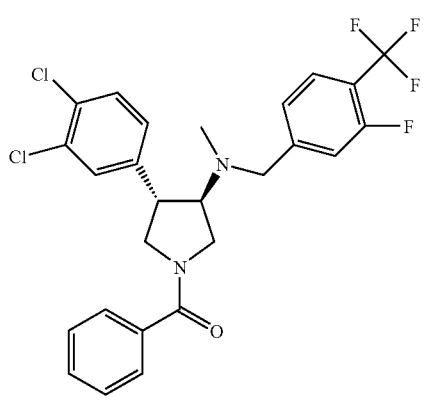

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: Benzoic acid (commercially available),
ES-MS m/e: 525.3 (M+H⁺).

EXAMPLE 6

4-{(3SR,4RS)-3-(3,4-Dichloro-phenyl)-4-[(3-fluoro-4-trifluoromethyl-benzyl)-methyl-amino]-pyrrolidine-1-carbonyl}-benzonitrile

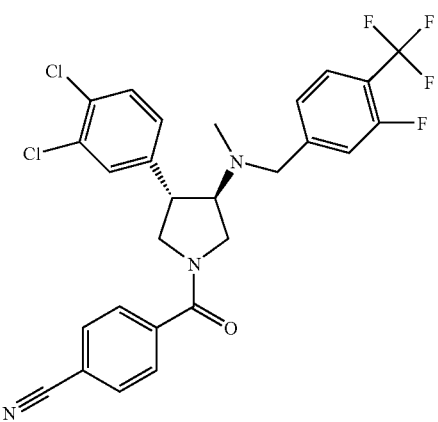

Coupling according to general procedure II:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Acid chlorid: 4-Cyano-benzoyl chloride (commercially available),
ES-MS m/e: 550.3 (M+H⁺).

EXAMPLE 7

{(3SR,4RS)-3-(3,4-Dichloro-phenyl)-4-[(3-fluoro-4-trifluoromethyl-benzyl)-methyl-amino]-pyrrolidin-1-yl}-(2-fluoro-3-trifluoromethyl-phenyl)-methanone

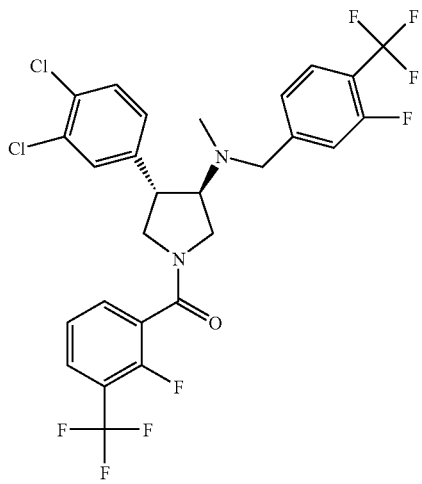

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Fluoro-3-trifluoromethyl-benzoic acid (commercially available),
ES-MS m/e: 611.1 (M+H⁺).

EXAMPLE 8

{(3SR,4RS)-3-(3,4-Dichloro-phenyl)-4-[(3-fluoro-4-trifluoromethyl-benzyl)-methyl-amino]-pyrrolidin-1-yl}-(2,3-difluoro-phenyl)-methanone

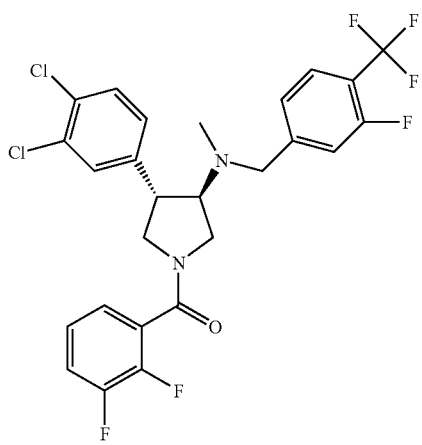

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2,3-Difluoro-benzoic acid (commercially available),
ES-MS m/e: 561.1 (M+H⁺).

EXAMPLE 9

3-{(3SR,4RS)-3-(3,4-Dichloro-phenyl)-4-[(3-fluoro-4-trifluoromethyl-benzyl)-methyl-amino]-pyrrolidine-1-carbonyl}-benzonitrile

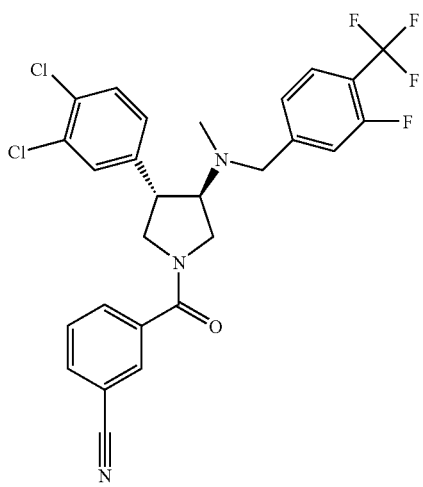

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 3-Cyano-benzoic acid (commercially available),
ES-MS m/e: 550.3 (M+H⁺).

EXAMPLE 10

{(3SR,4RS)-3-(3,4-Dichloro-phenyl)-4-[(3-fluoro-4-trifluoromethyl-benzyl)-methyl-amino]-pyrrolidin-1-yl}-(4-trifluoromethoxy-phenyl)-methanone

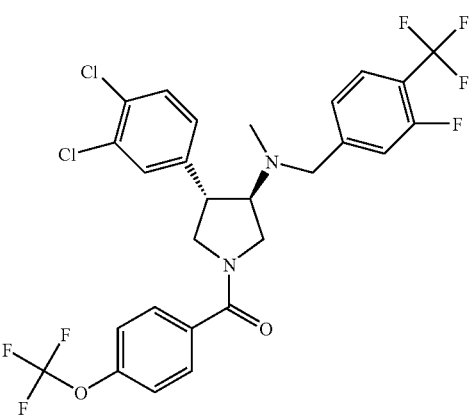

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Trifluoromethoxy-benzoic acid (commercially available), ES-MS m/e: 609.1 (M+H$^+$).

EXAMPLE 11

{(3SR,4RS)-3-(3,4-Dichloro-phenyl)-4-[(3-fluoro-4-trifluoromethyl-benzyl)-methyl-amino]-pyrrolidin-1-yl}-pyridin-3-yl-methanone

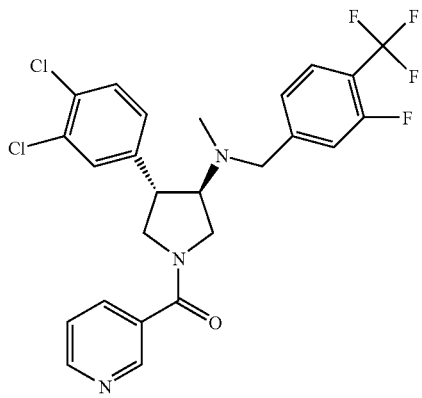

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: Nicotinic acid (commercially available), ES-MS m/e: 526.2 (M+H$^+$).

EXAMPLE 12

{(3SR,4RS)-3-(3,4-Dichloro-phenyl)-4-[(3-fluoro-4-trifluoromethyl-benzyl)-methyl-amino]-pyrrolidin-1-yl}-(5-methyl-isoxazol-3-yl)-methanone

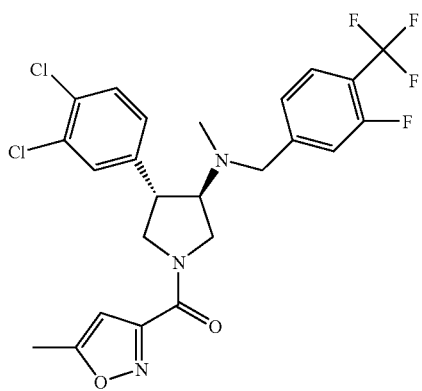

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 5-Methyl-isoxazole-3-carboxylic acid (commercially available), ES-MS m/e: 530.1 (M+H$^+$).

EXAMPLE 13

{(3SR,4RS)-3-(3,4-Dichloro-phenyl)-4-[(3-fluoro-4-trifluoromethyl-benzyl)-methyl-amino]-pyrrolidin-1-yl}-(2-methoxy-phenyl)-methanone

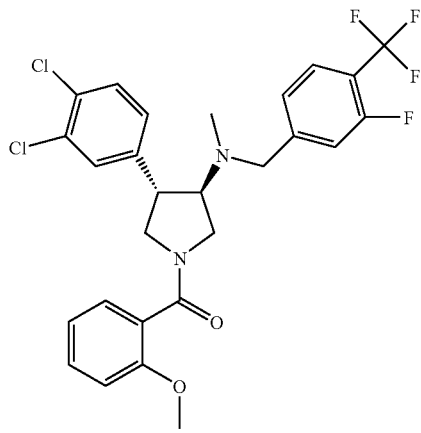

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2-Methoxy-benzoic acid (commercially available), ES-MS m/e: 555.2 (M+H$^+$).

EXAMPLE 14

{(3SR,4RS)-3-(3,4-Dichloro-phenyl)-4-[(3-fluoro-4-trifluoromethyl-benzyl)-methyl-amino]-pyrrolidin-1-yl}-m-tolyl-methanone

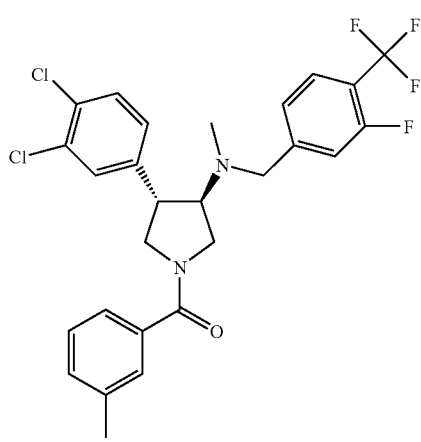

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 3-Methyl-benzoic acid (commercially available),
ES-MS m/e: 539.3 (M+H⁺).

EXAMPLE 15

{(3SR,4RS)-3-(3,4-Dichloro-phenyl)-4-[(3-fluoro-4-trifluoromethyl-benzyl)-methyl-amino]-pyrrolidin-1-yl}-(3,5-dimethoxy-phenyl)-methanone

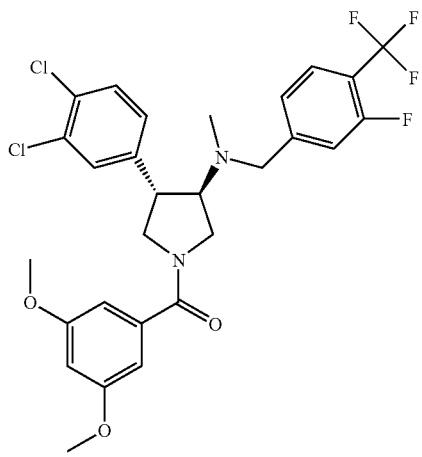

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 3,5-Dimethoxy-benzoic acid (commercially available),
ES-MS m/e: 585.2 (M+H⁺).

EXAMPLE 16

{(3SR,4RS)-3-(3,4-Dichloro-phenyl)-4-[(3-fluoro-4-trifluoromethyl-benzyl)-methyl-amino]-pyrrolidin-1-yl}-(3,4-dimethoxy-phenyl)-methanone

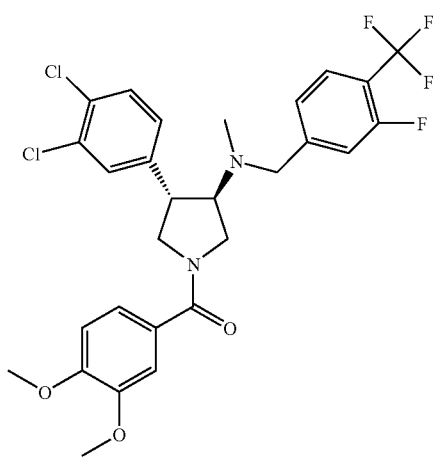

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 3,4-Dimethoxy-benzoic acid (commercially available),
ES-MS m/e: 585.2 (M+H⁺).

EXAMPLE 17

Benzo[1,3]dioxol-5-yl-{(3SR,4RS)-3-(3,4-dichloro-phenyl)-4-[(3-fluoro-4-trifluoromethyl-benzyl)-methyl-amino]-pyrrolidin-1-yl}-methanone

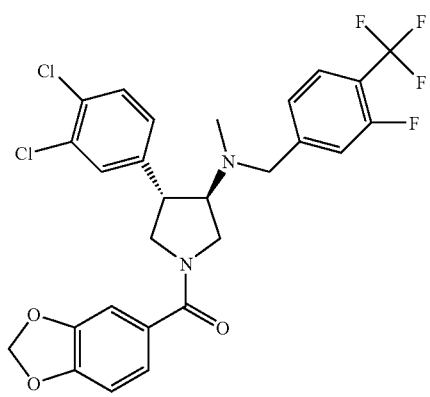

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: Benzo[1,3]dioxole-5-carboxylic acid (commercially available),
ES-MS m/e: 569.2 (M+H⁺).

EXAMPLE 18

4-({[(3RS,4SR)-1-(4-Cyano-benzoyl)-4-(3,4-dichloro-phenyl)-pyrrolidin-3-yl]-methyl-amino}-methyl)-2-fluoro-benzonitrile

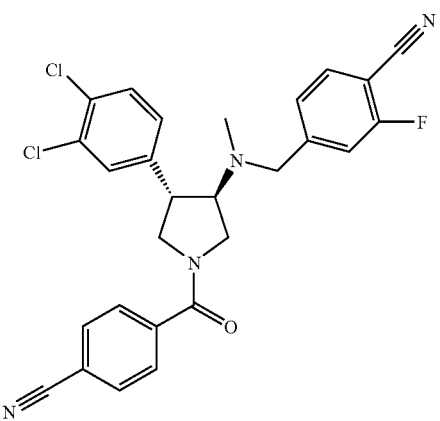

Reductive amination according to general procedure III:
Pyrrolidine intermediate: 4-[(3SR,4RS)-3-(3,4-Dichloro-phenyl)-4-methylamino-pyrrolidine-1-carbonyl]-benzonitrile (XII-3), Aldehyde: 2-Fluoro-4-formyl-benzonitrile (commercially available),
ES-MS m/e: 506.9 (M+H⁺).

EXAMPLE 19

4-{(3SR,4RS)-3-(3,4-Dichloro-phenyl)-4-[(3-fluoro-4-trifluoromethyl-benzyl)-methyl-amino]-pyrrolidine-1-carbonyl}-3-fluoro-benzonitrile

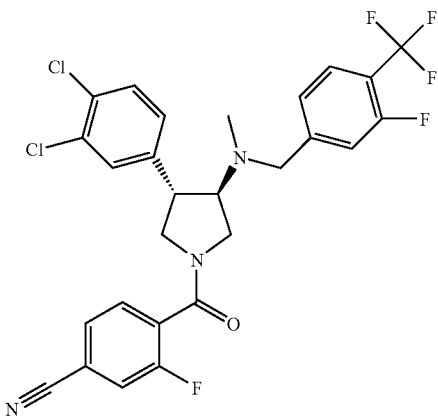

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Cyano-2-fluoro-benzoic acid (commercially available),
ES-MS m/e: 568.1 (M+H⁺).

EXAMPLE 20

{(3SR,4RS)-3-(3,4-Dichloro-phenyl)-4-[(3-fluoro-4-trifluoromethyl-benzyl)-methyl-amino]-pyrrolidin-1-yl}-(2-fluoro-5-methanesulfonyl-phenyl)-methanone

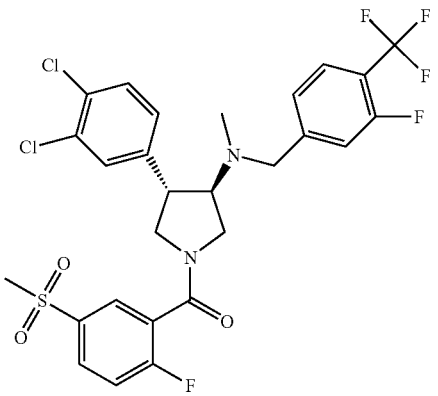

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Fluoro-5-methanesulfonyl-benzoic acid (described in the patent US20060149062),
ES-MS m/e: 621.1 (M+H⁺).

EXAMPLE 21

{(3SR,4RS)-3-(3,4-Dichloro-phenyl)-4-[(3-fluoro-4-trifluoromethyl-benzyl)-methyl-amino]-pyrrolidin-1-yl}-(5-ethanesulfonyl-2-fluoro-phenyl)-methanone

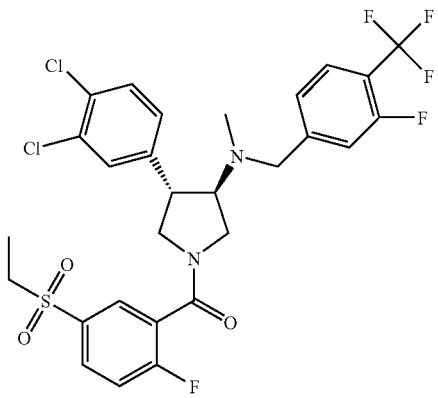

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 5-Ethanesulfonyl-2-fluoro-benzoic acid (described in the patent WO2006072436),
ES-MS m/e: 635.1 (M+H⁺).

EXAMPLE 22

{(3SR,4RS)-3-(3,4-Dichloro-phenyl)-4-[(3-fluoro-4-trifluoromethyl-benzyl)-methyl-amino]-pyrrolidin-1-yl}-(4-methanesulfonyl-phenyl)-methanone

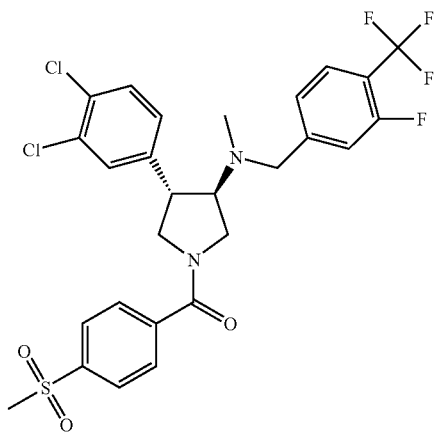

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Methanesulfonyl-benzoic acid (commercially available),
ES-MS m/e: 603.1 (M+H+).

EXAMPLE 23

4-{(3SR,4RS)-3-(3,4-Dichloro-phenyl)-4-[(3-fluoro-4-trifluoromethyl-benzyl)-methyl-amino]-pyrrolidine-1-carbonyl}-2-methyl-benzonitrile

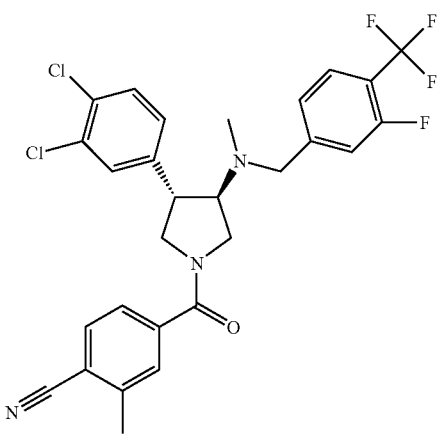

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Cyano-3-methyl-benzoic acid (preparation described in Bioorg. Med./Chem. Lett. 14 (2004) 4585-4589),
ES-MS m/e: 566.1 (M+H+).

EXAMPLE 24

1-(4-{(3SR,4RS)-3-(3,4-Dichloro-phenyl)-4-[(3-fluoro-4-trifluoromethyl-benzyl)-methyl-amino]-pyrrolidine-1-carbonyl}-phenyl)-ethanone

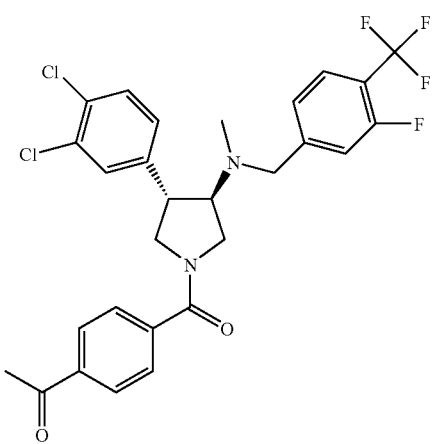

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Acetyl-benzoic acid (commercially available),
ES-MS m/e: 567.2 (M+H+).

EXAMPLE 25

{(3SR,4RS)-3-(3,4-Dichloro-phenyl)-4-[(3-fluoro-4-trifluoromethyl-benzyl)-methyl-amino]-pyrrolidin-1-yl}-(6-methyl-pyridin-3-yl)-methanone

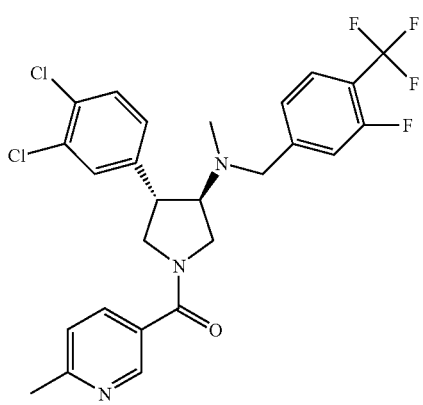

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-Methyl-nicotinic acid (commercially available),
ES-MS m/e: 540.1 (M+H+).

EXAMPLE 26

5-{(3SR,4RS)-3-(3,4-Dichloro-phenyl)-4-[(3-fluoro-4-trifluoromethyl-benzyl)-methyl-amino]-pyrrolidine-1-carbonyl}-pyridine-2-carbonitrile

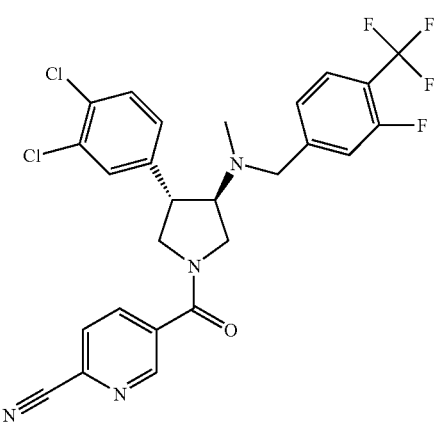

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Cyano-nicotinic acid (commercially available),
ES-MS m/e: 551.1 (M+H$^+$).

EXAMPLE 27

{(3SR,4RS)-3-(3,4-Dichloro-phenyl)-4-[(3-fluoro-4-trifluoromethyl-benzyl)-methyl-amino]-pyrrolidin-1-yl}-(6-morpholin-4-yl-pyridin-3-yl)-methanone

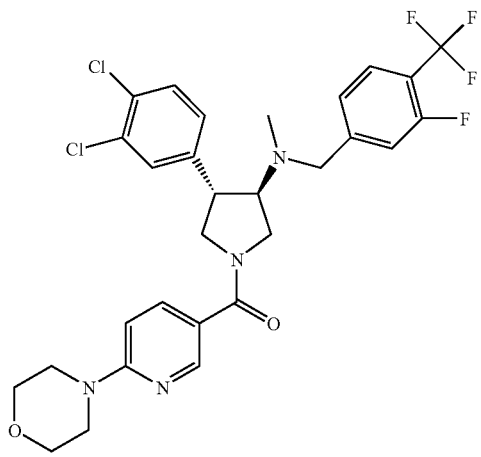

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-Morpholin-4-yl-nicotinic acid (commercially available),
ES-MS m/e: 611.2 (M+H$^+$).

EXAMPLE 28

{(3SR,4RS)-3-(3,4-Dichloro-phenyl)-4-[(3-fluoro-4-trifluoromethyl-benzyl)-methyl-amino]-pyrrolidin-1-yl}-(6-fluoro-pyridin-3-yl)-methanone

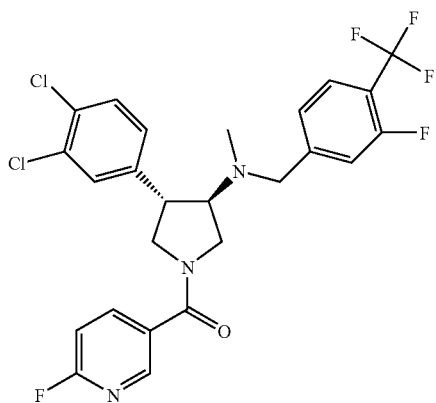

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-Fluoro-nicotinic acid (commercially available),
ES-MS m/e: 546.2 (M+H$^+$).

EXAMPLE 29

{(3SR,4RS)-3-(3,4-Dichloro-phenyl)-4-[(3-fluoro-4-trifluoromethyl-benzyl)-methyl-amino]-pyrrolidin-1-yl}-(6-methoxy-pyridin-3-yl)-methanone

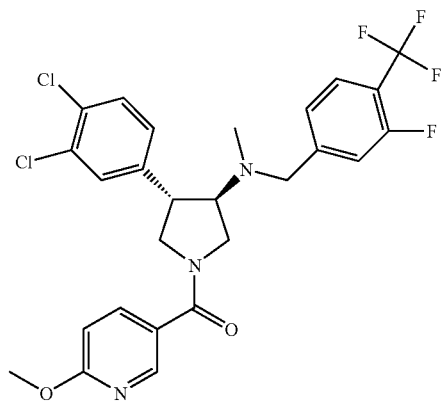

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-Methoxy-nicotinic acid (commercially available),
ES-MS m/e: 556.1 (M+H$^+$).

EXAMPLE 30

{(3SR,4RS)-3-(3,4-Dichloro-phenyl)-4-[(3-fluoro-4-trifluoromethyl-benzyl)-methyl-amino]-pyrrolidin-1-yl}-(6-pyrazol-1-yl-pyridin-3-yl)-methanone

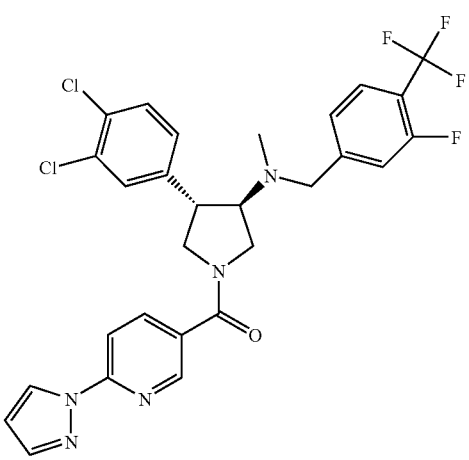

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Pyrazol-1-yl-nicotinic acid (commercially available),
ES-MS m/e: 592.1 (M+H⁺).

EXAMPLE 31

{(3SR,4RS)-3-(3,4-Dichloro-phenyl)-4-[(3-fluoro-4-trifluoromethyl-benzyl)-methyl-amino]-pyrrolidin-1-yl}-p-tolyl-methanone

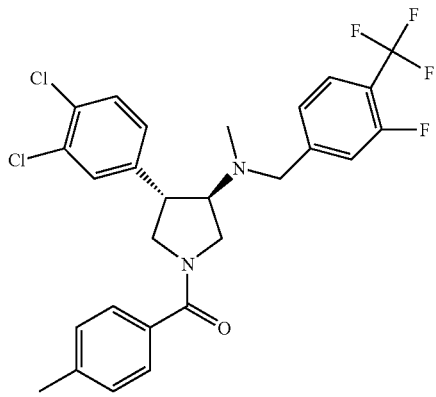

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Methyl-benzoic acid (commercially available),
ES-MS m/e: 539.2 (M+H⁺).

EXAMPLE 32

{(3SR,4RS)-3-(3,4-Dichloro-phenyl)-4-[(3-fluoro-4-trifluoromethyl-benzyl)-methyl-amino]-pyrrolidin-1-yl}-(2-morpholin-4-yl-pyridin-4-yl)-methanone

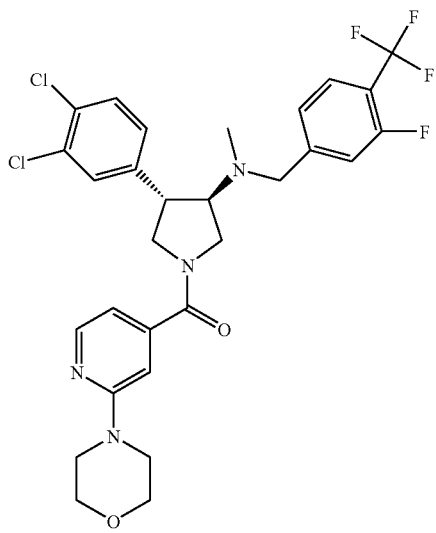

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2-Morpholin-4-yl-isonicotinic acid (commercially available),
ES-MS m/e: 611.2 (M+H⁺).

EXAMPLE 33

{(3SR,4RS)-3-(3,4-Dichloro-phenyl)-4-[(3-fluoro-4-trifluoromethyl-benzyl)-methyl-amino]-pyrrolidin-1-yl}-(2-methyl-pyridin-4-yl)-methanone

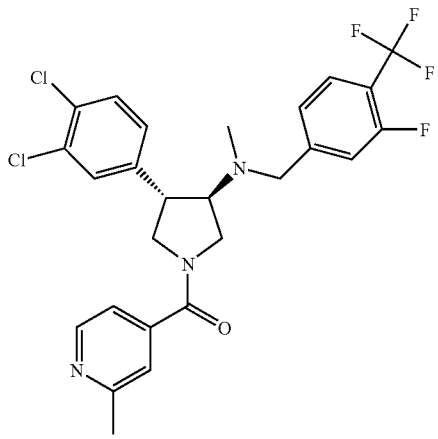

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Methyl-isonicotinic acid (commercially available),
ES-MS m/e: 542.2 (M+H⁺).

EXAMPLE 34

N-(4-{(3SR,4RS)-3-(3,4-Dichloro-phenyl)-4-[(3-fluoro-4-trifluoromethyl-benzyl)-methyl-amino]-pyrrolidine-1-carbonyl}-pyridin-2-yl)-acetamide

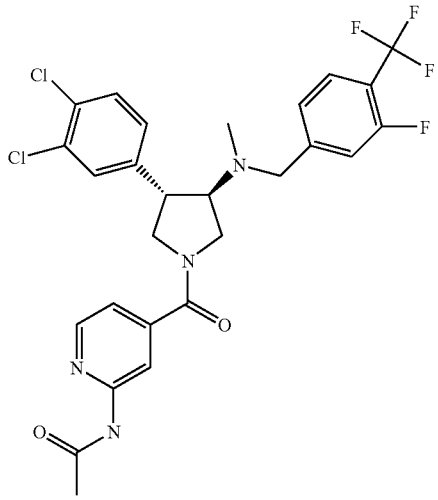

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2-Acetylamino-isonicotinic acid (commercially available),
ES-MS m/e: 583.2 (M+H$^+$).

EXAMPLE 35

{(3SR,4RS)-3-(3,4-Dichloro-phenyl)-4-[(3-fluoro-4-trifluoromethyl-benzyl)-methyl-amino]-pyrrolidin-1-yl}-(2-methoxy-pyridin-4-yl)-methanone

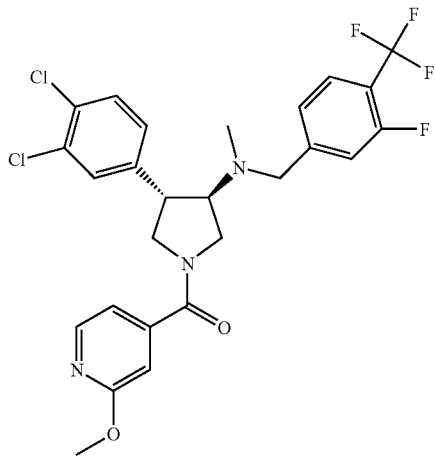

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Methoxy-isonicotinic acid (commercially available),
ES-MS m/e: 556.2 (M+H$^+$).

EXAMPLE 36

(4-Chloro-phenyl)-{(3SR,4RS)-3-(3,4-dichloro-phenyl)-4-[(3-fluoro-4-trifluoromethyl-benzyl)-methyl-amino]-pyrrolidin-1-yl}-methanone

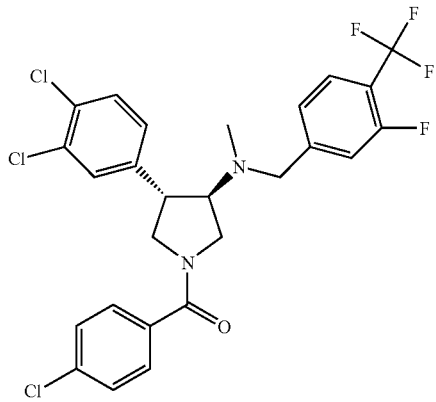

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Chloro-benzoic acid (commercially available),
ES-MS m/e: 561.1 (M+H$^+$).

EXAMPLE 37

{(3SR,4RS)-3-(3,4-Dichloro-phenyl)-4-[(3-fluoro-4-trifluoromethyl-benzyl)-methyl-amino]-pyrrolidin-1-yl}-(2-fluoro-5-methyl-phenyl)-methanone

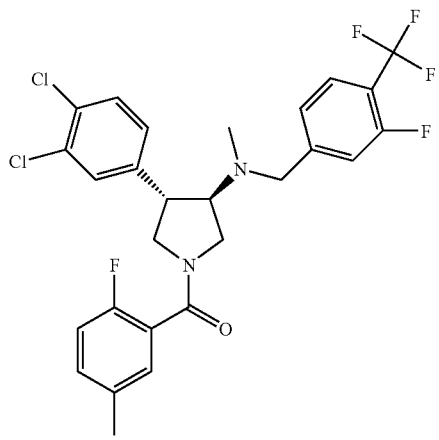

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Fluoro-5-methyl-benzoic acid (commercially available),
ES-MS m/e: 557.1 (M+H$^+$).

EXAMPLE 38

{(3SR,4RS)-3-(3,4-Dichloro-phenyl)-4-[(3-fluoro-4-trifluoromethyl-benzyl)-methyl-amino]-pyrrolidin-1-yl}-(4-morpholin-4-yl-phenyl)-methanone

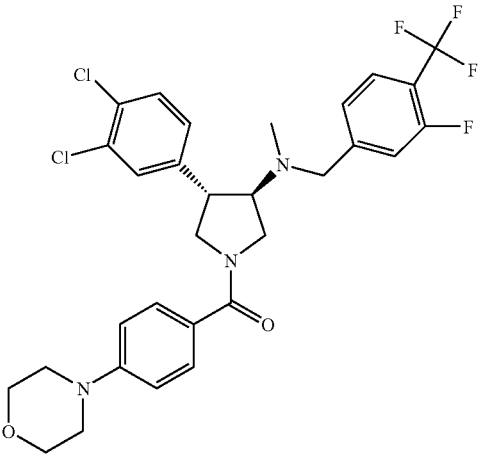

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Morpholin-4-yl-benzoic acid (commercially available),
ES-MS m/e: 609.6 (M+H⁺).

EXAMPLE 39

2-(4-{(3SR,4RS)-3-(3,4-Dichloro-phenyl)-4-[(3-fluoro-4-trifluoromethyl-benzyl)-methyl-amino]-pyrrolidine-1-carbonyl}-phenyl)-5-methyl-2,4-dihydro-pyrazol-3-one

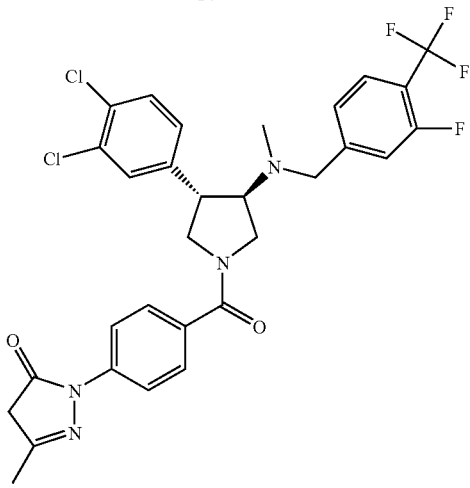

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-(3-Methyl-5-oxo-4,5-dihydro-pyrazol-1-yl)-benzoic acid (commercially available),
ES-MS m/e: 620.7 (M+H⁺).

EXAMPLE 40

{(3SR,4RS)-3-(3,4-Dichloro-phenyl)-4-[(3-fluoro-4-trifluoromethyl-benzyl)-methyl-amino]-pyrrolidin-1-yl}-(4-[1,2,4]triazol-1-yl-phenyl)-methanone

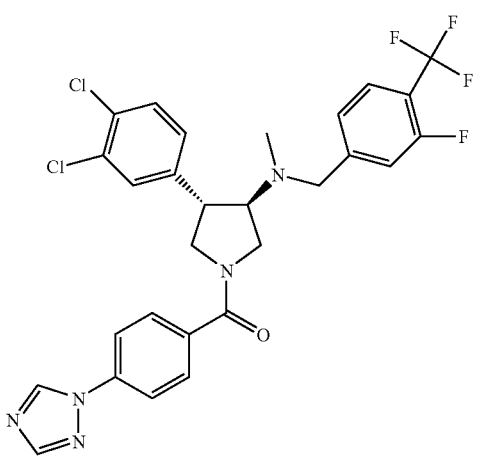

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-[1,2,4]Triazol-1-yl-benzoic acid (commercially available),
ES-MS m/e: 591.8 (M+H⁺).

EXAMPLE 41

{(3SR,4RS)-3-(3,4-Dichloro-phenyl)-4-[(3-fluoro-4-trifluoromethyl-benzyl)-methyl-amino]-pyrrolidin-1-yl}-(4-imidazol-1-yl-phenyl)-methanone

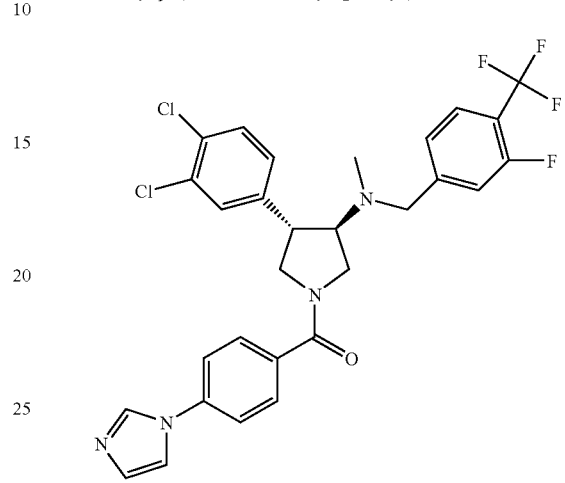

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Imidazol-1-yl-benzoic acid (commercially available),
ES-MS m/e: 590.8 (M+H⁺).

EXAMPLE 42

{(3SR,4RS)-3-(3,4-Dichloro-phenyl)-4-[(3-fluoro-4-trifluoromethyl-benzyl)-methyl-amino]-pyrrolidin-1-yl}-[4-(1,1-dioxo-1-6-isothiazolidin-2-yl)-phenyl]-methanone

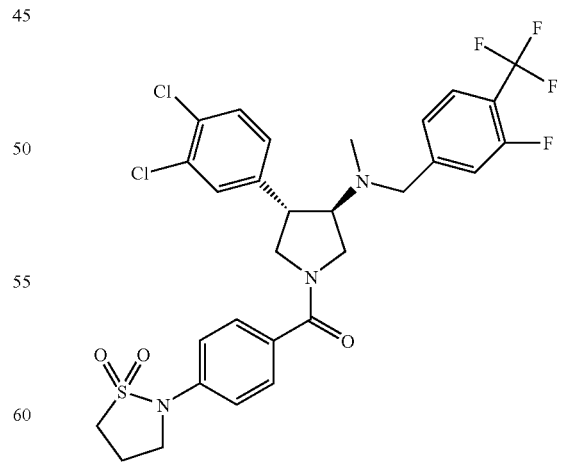

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-(1,1-Dioxo-1-6-isothiazolidin-2-yl)-benzoic acid (commercially available),
ES-MS m/e: 643.8 (M+H+).

EXAMPLE 43

{(3SR,4RS)-3-(3,4-Dichloro-phenyl)-4-[(3-fluoro-4-trifluoromethyl-benzyl)-methyl-amino]-pyrrolidin-1-yl}-(4-pyridin-2-yl-phenyl)-methanone

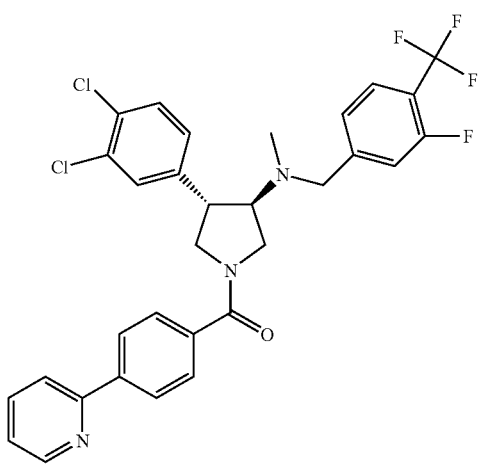

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Pyridin-2-yl-benzoic acid (commercially available),
ES-MS m/e: 601.8 (M+H+).

EXAMPLE 44

{(3SR,4RS)-3-(3,4-Dichloro-phenyl)-4-[(3-fluoro-4-trifluoromethyl-benzyl)-methyl-amino]-pyrrolidin-1-yl}-(4-pyridin-3-yl-phenyl)-methanone

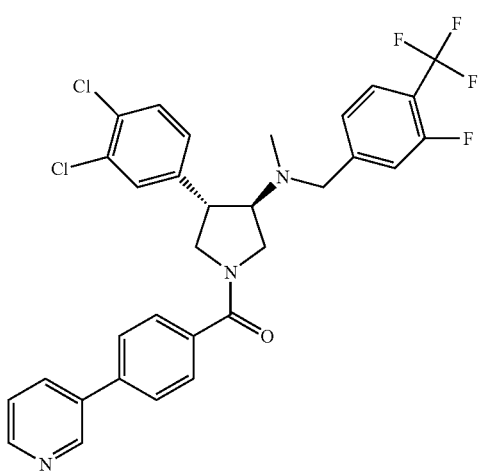

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Pyridin-3-yl-benzoic acid (commercially available),
ES-MS m/e: 601.8 (M+H+).

EXAMPLE 45

{(3SR,4RS)-3-(3,4-Dichloro-phenyl)-4-[(3-fluoro-4-trifluoromethyl-benzyl)-methyl-amino]-pyrrolidin-1-yl}-(4-pyridin-4-yl-phenyl)-methanone

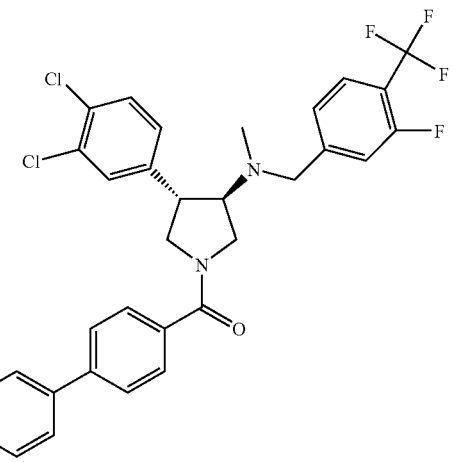

Amid coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Pyridin-4-yl-benzoic acid (commercially available),
ES-MS m/e: 601.8 (M+H+).

EXAMPLE 46

(6-Amino-pyridin-3-yl)-{(3SR,4RS)-3-(3,4-dichloro-phenyl)-4-[(3-fluoro-4-trifluoromethyl-benzyl)-methyl-amino]-pyrrolidin-1-yl}-methanone

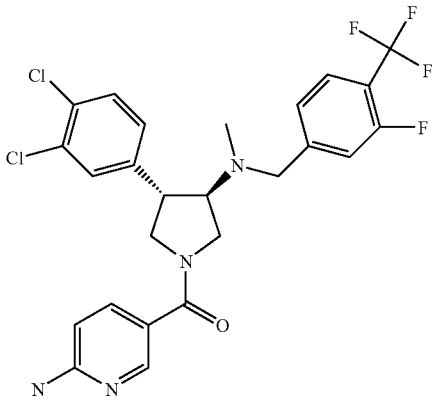

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Amino-nicotinic acid (commercially available),
ES-MS m/e: 540.8 (M+H+).

EXAMPLE 47

{(3SR,4RS)-3-(3,4-Dichloro-phenyl)-4-[(3-fluoro-4-trifluoromethyl-benzyl)-methyl-amino]-pyrrolidin-1-yl}-(4-[1,3,4]oxadiazol-2-yl-phenyl)-methanone

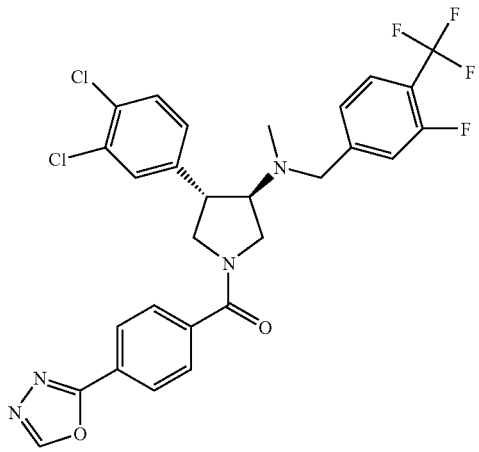

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-[1,3,4]Oxadiazol-2-yl-benzoic acid (commercially available),
ES-MS m/e: 592.9 (M+H+).

EXAMPLE 48

{(3SR,4RS)-3-(3,4-Dichloro-phenyl)-4-[(3-fluoro-4-trifluoromethyl-benzyl)-methyl-amino]-pyrrolidin-1-yl}-(6-hydroxy-pyridin-3-yl)-methanone

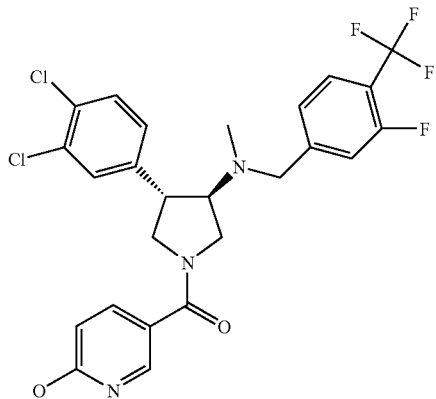

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Hydroxy-nicotinic acid (commercially available),
ES-MS m/e: 542.1 (M+H+).

EXAMPLE 49

{(3SR,4RS)-3-(3,4-Dichloro-phenyl)-4-[(3-fluoro-4-trifluoromethyl-benzyl)-methyl-amino]-pyrrolidin-1-yl}-(2-hydroxy-pyridin-4-yl)-methanone

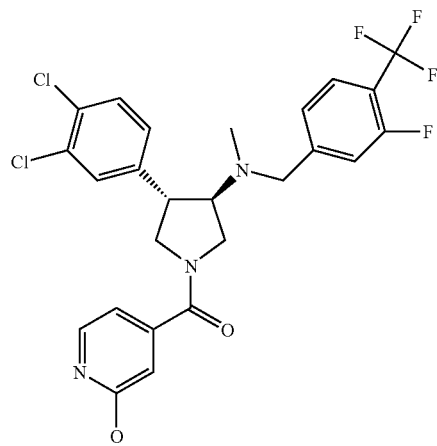

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 2-Hydroxy-isonicotinic acid (commercially available),
ES-MS m/e: 542.1 (M+H+).

EXAMPLE 50

(5-Amino-pyridin-2-yl)-{(3SR,4RS)-3-(3,4-dichloro-phenyl)-4-[(3-fluoro-4-trifluoromethyl-benzyl)-methyl-amino]-pyrrolidin-1-yl}-methanone

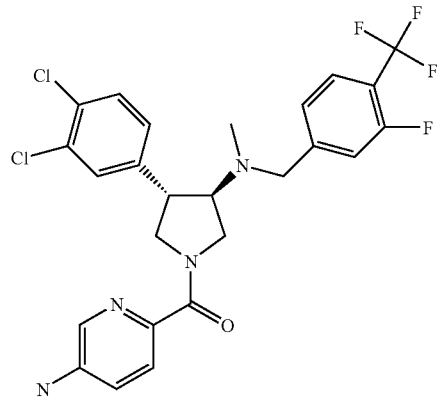

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 5-Amino-pyridine-2-carboxylic acid (commercially available), ES-MS m/e: 541.2 (M+H⁺).

EXAMPLE 51

{(3SR,4RS)-3-(3,4-Dichloro-phenyl)-4-[(3-fluoro-4-trifluoromethyl-benzyl)-methyl-amino]-pyrrolidin-1-yl}-[1,6]naphthyridin-2-yl-methanone

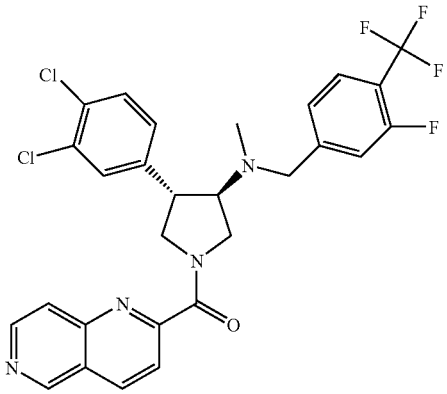

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: [1,6]Naphthyridine-2-carboxylic acid (commercially available), ES-MS m/e: 577.4 (M+H⁺).

EXAMPLE 52

{(3SR,4RS)-3-(3,4-Dichloro-phenyl)-4-[(3-fluoro-4-trifluoromethyl-benzyl)-methyl-amino]-pyrrolidin-1-yl}-pyrimidin-4-yl-methanone

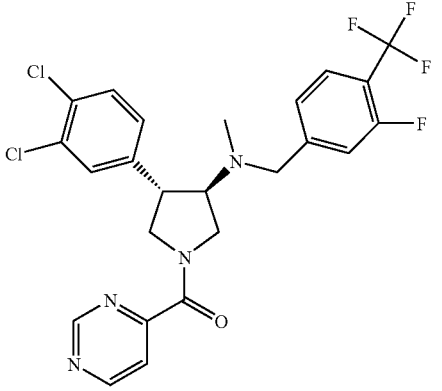

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: Pyrimidine-4-carboxylic acid (commercially available), ES-MS m/e: 527.3 (M+H⁺).

EXAMPLE 53

(2-Amino-5-chloro-pyrimidin-4-yl)-{(3SR,4RS)-3-(3,4-dichloro-phenyl)-4-[(3-fluoro-4-trifluoromethyl-benzil)-methyl-amino]-pyrrolidin-1-yl}-methanone

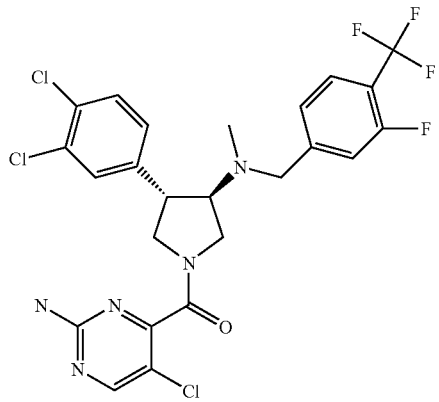

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2-Amino-5-chloro-pyrimidine-4-carboxylic acid (commercially available), ES-MS m/e: 576.8 (M+H⁺).

EXAMPLE 54

{(3SR,4RS)-3-(3,4-Dichloro-phenyl)-4-[(3-fluoro-4-trifluoromethyl-benzyl)-methyl-amino]-pyrrolidin-1-yl}-pyrazin-2-yl-methanone

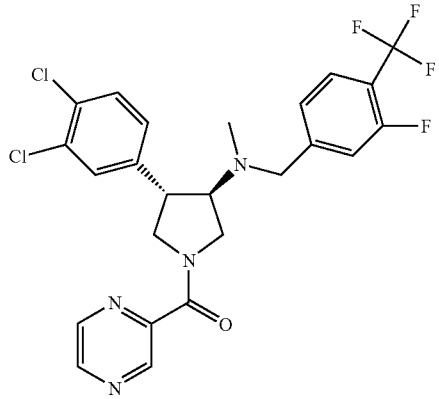

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: Pyrazine-2-carboxylic acid (commercially available),
ES-MS m/e: 527.3 (M+H$^+$).

EXAMPLE 55

{(3SR,4RS)-3-(3,4-Dichloro-phenyl)-4-[(3-fluoro-4-trifluoromethyl-benzyl)-methyl-amino]-pyrrolidin-1-yl}-(5-methyl-pyrazin-2-yl)-methanone

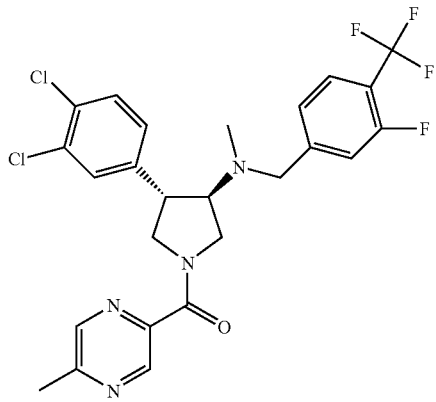

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 5-Methyl-pyrazine-2-carboxylic acid (commercially available), ES-MS m/e: 541.4 (M+H$^+$).

EXAMPLE 56

{(3SR,4RS)-3-(3,4-Dichloro-phenyl)-4-[(3-fluoro-4-trifluoromethyl-benzyl)-methyl-amino]-pyrrolidin-1-yl}-(6-methoxy-pyrazin-2-yl)-methanone

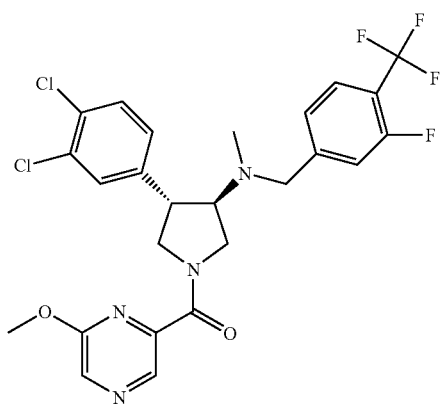

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 6-Methoxy-pyrazine-2-carboxylic acid (commercially available),
ES-MS m/e: 557.4 (M+H$^+$).

EXAMPLE 57

{(3SR,4RS)-3-(3,4-Dichloro-phenyl)-4-[(3-fluoro-4-trifluoromethyl-benzyl)-methyl-amino]-pyrrolidin-1-yl}-(2-methoxy-pyrimidin-5-yl)-methanone

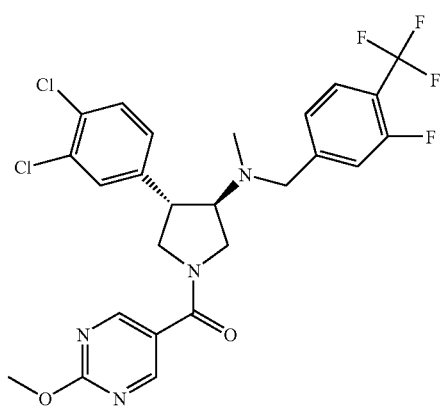

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 2-Methoxy-pyrimidine-5-carboxylic acid (commercially available), ES-MS m/e: 557.4 (M+H$^+$).

EXAMPLE 58

{(3SR,4RS)-3-(3,4-Dichloro-phenyl)-4-[(3-fluoro-4-trifluoromethyl-benzyl)-methyl-amino]-pyrrolidin-1-yl}-(4-methylamino-phenyl)-methanone

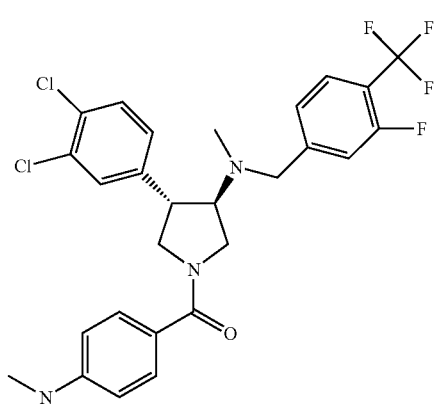

Amide coupling according to general procedure I:

Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 4-Methylamino-benzoic acid (commercially available),
ES-MS m/e: 554.4 (M+H⁺).

EXAMPLE 59

(3H-Benzotriazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone

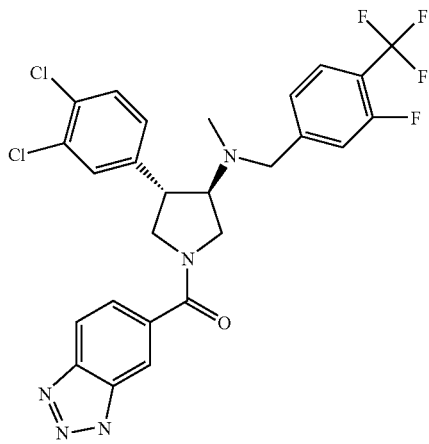

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 3H-Benzotriazole-5-carboxylic acid (commercially available),
ES-MS m/e: 566.4 (M+H⁺).

EXAMPLE 60

(3H-Benzoimidazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone

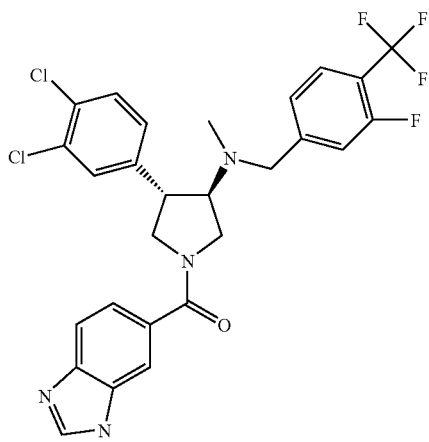

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 3H-Benzoimidazole-5-carboxylic acid (commercially available),
ES-MS m/e: 564.4 (M+H⁺).

EXAMPLE 61

N-(4-{(3SR,4RS)-3-(3,4-Dichloro-phenyl)-4-[(3-fluoro-4-trifluoromethyl-benzyl)-methyl-amino]-pyrrolidine-1-carbonyl}-phenyl)-acetamide

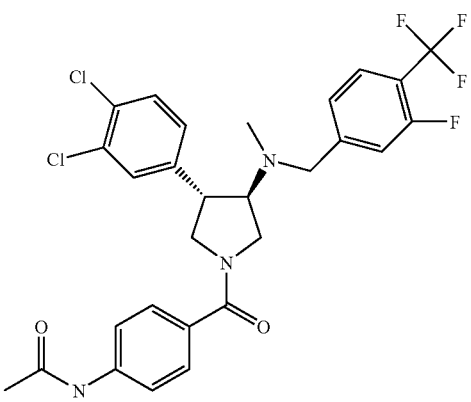

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Acetylamino-benzoic acid (commercially available),
ES-MS m/e: 582.4 (M+H⁺).

EXAMPLE 62

{(3S,4R)-3-(3,4-Dichloro-phenyl)-4-[(3-fluoro-4-trifluoromethyl-benzyl)-methyl-amino]-pyrrolidin-1-yl}-(3H-imidazo[4,5-b]pyridin-6-yl)-methanone

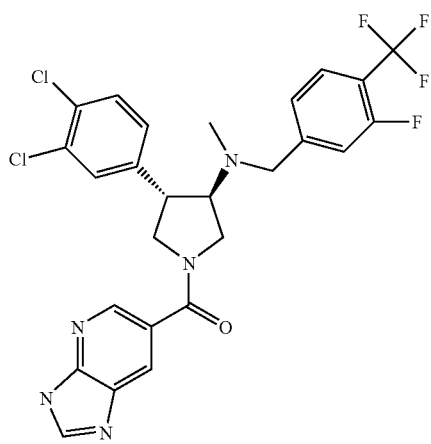

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1), Carboxylic acid: 3H-Imidazo[4,5-b]pyridine-6-carboxylic acid (commercially available),
ES-MS m/e: 566.4 (M+H⁺).

EXAMPLE 63

4-(5-{(3SR,4RS)-3-(3,4-Dichloro-phenyl)-4-[(3-fluoro-4-trifluoromethyl-benzyl)-methyl-amino]-pyrrolidine-1-carbonyl}-pyridin-2-yl)-piperazine-1-carboxylic acid tert-butyl ester

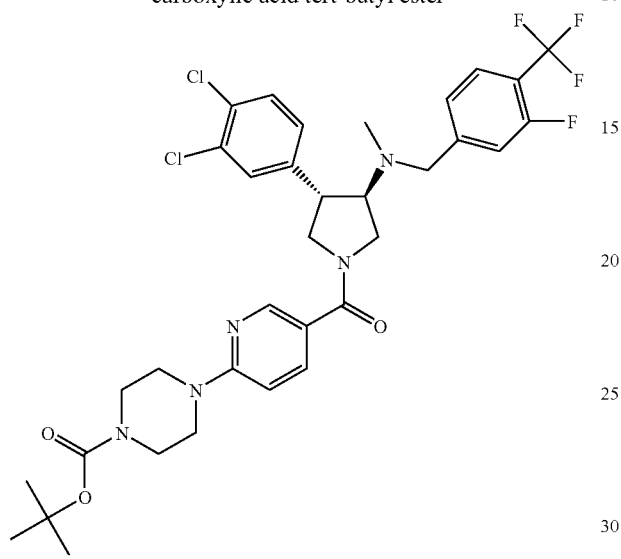

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-(5-Carboxy-pyridin-2-yl)-piperazine-1-carboxylic acid tert-butyl ester (commercially available),
ES-MS m/e: 710.4 (M+H⁺).

EXAMPLE 64

{(3SR,4RS)-3-(3,4-Dichloro-phenyl)-4-[(3-fluoro-4-trifluoromethyl-benzyl)-methyl-amino]-pyrrolidin-1-yl}-[6-(1,1-dioxo-1-6-thiomorpholin-4-yl)-pyridin-3-yl]-methanone

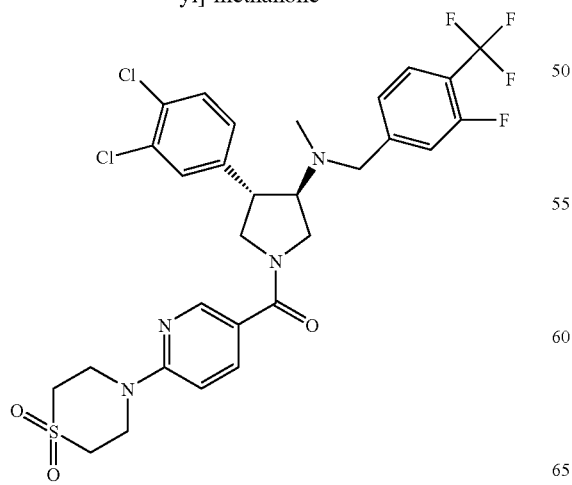

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-(1,1-Dioxo-1-6-thiomorpholin-4-yl)-nicotinic acid (commercially available),
ES-MS m/e: 659.5 (M+H⁺).

EXAMPLE 65

{(3SR,4RS)-3-(3,4-Dichloro-phenyl)-4-[(3-fluoro-4-trifluoromethyl-benzyl)-methyl-amino]-pyrrolidin-1-yl}-(6-piperazin-1-yl-pyridin-3-yl)-methanone

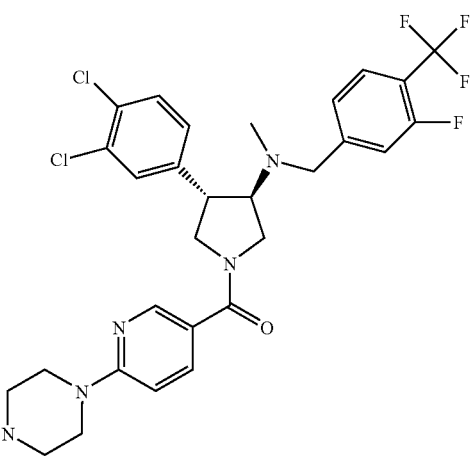

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 6-piperazin-1-yl-nicotinic acid (commercially available),
ES-MS m/e: 610.5 (M+H⁺).

EXAMPLE 66

4-{(3SR,4RS)-3-(4-Chloro-3-fluoro-phenyl)-4-[(3-fluoro-4-trifluoromethyl-benzyl)-methyl-amino]-pyrrolidine-1-carbonyl}-benzonitrile

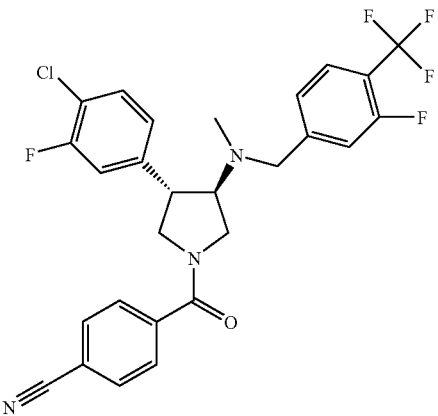

Amide coupling according to general procedure I:
Pyrrolidine intermediate: [(3RS,4SR)-4-(4-Chloro-3-fluoro-phenyl)-pyrrolidin-3-yl]-(3-fluoro-4-trifluoromethyl-benzyl)-methyl-amine (VIII-3), Carboxylic acid: 4-Cyano-benzoic acid (commercially available),
ES-MS m/e: 533.8 (M+H⁺).

EXAMPLE 67

{(3SR,4RS)-3-(3,4-Dichloro-phenyl)-4-[(3-fluoro-4-trifluoromethyl-benzyl)-methyl-amino]-pyrrolidin-1-yl}-(4-oxazol-5-yl-phenyl)-methanone

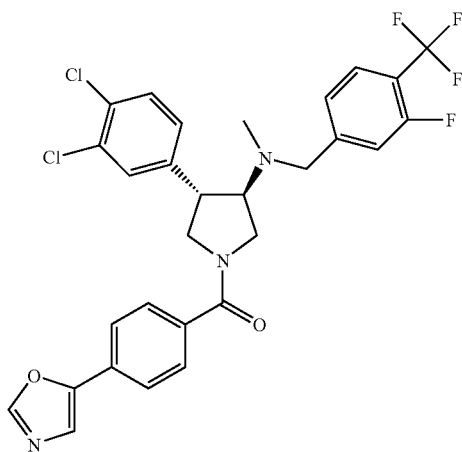

Amide coupling according to general procedure I:
Pyrrolidine intermediate: [(3RS,4SR)-4-(3,4-Dichloro-phenyl)-pyrrolidin-3-yl]-(3-fluoro-4-trifluoromethyl-benzyl)-methyl-amine (VIII-1),
Carboxylic acid: 4-Oxazol-5-yl-benzoic acid (commercially available),
ES-MS m/e: 592.3 (M+H⁺).

EXAMPLE 68

4-{(3SR,4RS)-3-(3,4-Dichloro-phenyl)-4-[methyl-(4-trifluoromethyl-benzyl)-amino]-pyrrolidine-1-carbonyl}-benzonitrile

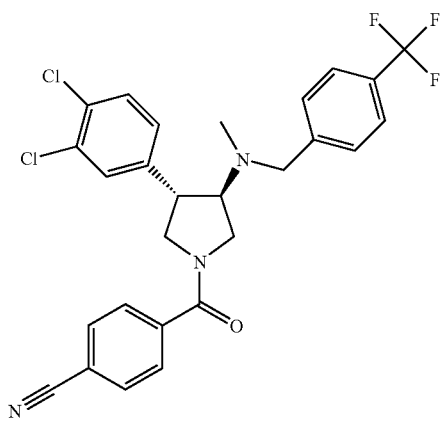

Amide coupling according to general procedure I:
Pyrrolidine intermediate: [(3RS,4SR)-4-(3,4-Dichloro-phenyl)-pyrrolidin-3-yl]-methyl-(4-trifluoromethyl-benzyl)-amine (VIII-2), Carboxylic acid: 4-Cyano-benzoic acid (commercially available),
ES-MS m/e: 531.8 (M+H⁺).

EXAMPLE 69

4-{(3SR,4RS)-3-(3-Chloro-phenyl)-4-[(3-fluoro-4-trifluoromethyl-benzyl)-methyl-amino]-pyrrolidine-1-carbonyl}-benzonitrile

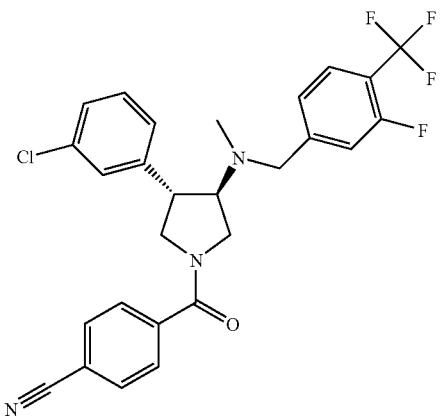

Amide coupling according to general procedure I:
Pyrrolidine intermediate: [(3RS,4SR)-4-(3-Chloro-phenyl)-pyrrolidin-3-yl]-(3-fluoro-4-trifluoromethyl-benzyl)-methyl-amine (VIII-4),
Carboxylic acid: 4-Cyano-benzoic acid (commercially available),
ES-MS m/e: 516.0 (M+H⁺).

EXAMPLE 70

4-{(3SR,4RS)-3-(3-Chloro-phenyl)-4-[methyl-(4-trifluoromethyl-benzyl)-amino]-pyrrolidine-1-carbonyl}-benzonitrile

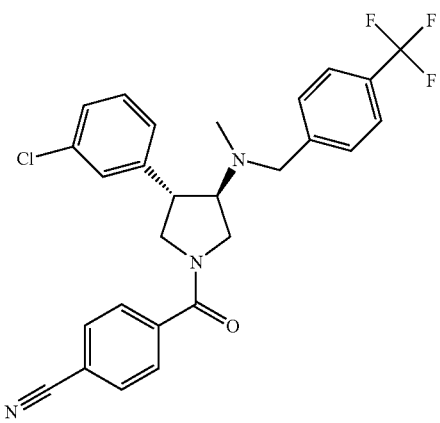

Amide coupling according to general procedure I:
Pyrrolidine intermediate: [(3RS,4SR)-4-(3-Chloro-phenyl)-pyrrolidin-3-yl]-methyl-(4-trifluoromethyl-benzyl)-amine (VIII-5),
Carboxylic acid: 4-Cyano-benzoic acid (commercially available),
ES-MS m/e: 498.0 (M+H⁺).

The invention claimed is:
1. A compound of formula I

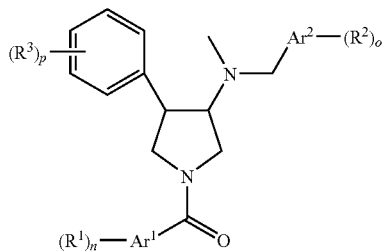

wherein
Ar¹ is aryl or heteroaryl;
Ar² is aryl or heteroaryl;
R¹ is hydrogen, halogen, hydroxy, lower alkyl, lower alkoxy, lower alkyl substituted by halogen, lower alkoxy substituted by halogen, S-lower alkyl, —S(O)₂-lower alkyl, —S(O)₂-di-lower alkyl amino, cyano, amino, mono or di-lower alkyl amino, C(O)-lower alkyl, NHC(O)-lower alkyl, cycloalkyl, heterocyclyl, or heteroaryl optionally substituted by lower alkyl;
R² is hydrogen, halogen, lower alkyl, lower alkoxy, lower alkyl substituted by halogen or cyano;
R³ is hydrogen, halogen, lower alkyl or lower alkyl substituted by halogen;
n is 1, 2 or 3; wherein when n is 2 or 3, each R¹ is the same or different;
o is 1, 2 or 3; wherein when o is 2 or 3, each R² is the same or different; and
p is 1, 2 or 3; wherein when p is 2 or 3, each R⁴ is the same or different;
or a pharmaceutically active salt, a racemic mixture, an enantiomer, an optical isomer or a tautomeric form thereof.

2. The compound of claim 1, wherein Ar¹ is aryl and Ar² is phenyl.

3. The compound of claim 2, selected from the group consisting of
4-{(3SR,4RS)-3-(3,4-dichloro-phenyl)-4-[(3-fluoro-4-trifluoromethyl-benzyl)-methyl-amino]-pyrrolidine-1-carbonyl}-benzonitrile;
3-{(3SR,4RS)-3-(3,4-dichloro-phenyl)-4-[(3-fluoro-4-trifluoromethyl-benzyl)-methyl-amino]-pyrrolidine-1-carbonyl}-benzonitrile;
4-({[(3RS,4SR)-1-(4-cyano-benzoyl)-4-(3,4-dichloro-phenyl)-pyrrolidin-3-yl]-methyl-amino}-methyl)-2-fluoro-benzonitrile;
4-{(3SR,4RS)-3-(3,4-dichloro-phenyl)-4-[(3-fluoro-4-trifluoromethyl-benzyl)-methyl-amino]-pyrrolidine-1-carbonyl}-3-fluoro-benzonitrile;
{(3SR,4RS)-3-(3,4-dichloro-phenyl)-4-[(3-fluoro-4-trifluoromethyl-benzyl)-methyl-amino]-pyrrolidin-1-yl}-(2-fluoro-5-methanesulfonyl-phenyl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-methanesulfonyl-phenyl)-methanone;
4-{(3SR,4RS)-3-(3,4-dichloro-phenyl)-4-[(3-fluoro-4-trifluoromethyl-benzyl)-methyl-amino]-pyrrolidine-1-carbonyl}-2-methyl-benzonitrile;
1-(4-{(3SR,4RS)-3-(3,4-dichloro-phenyl)-4-[(3-fluoro-4-trifluoromethyl-benzyl)-methyl-amino]-pyrrolidine-1-carbonyl}-phenyl)-ethanone;
{(3SR,4RS)-3-(3,4-dichloro-phenyl)-4-[(3-fluoro-4-trifluoromethyl-benzyl)-methyl-amino]-pyrrolidin-1-yl}-(4-morpholin-4-yl-phenyl)-methanone; and
{(3SR,4RS)-3-(3,4-dichloro-phenyl)-4-[(3-fluoro-4-trifluoromethyl-benzyl)-methyl-amino]-pyrrolidin-1-yl}-(4-[1,2,4]triazol-1-yl-phenyl)-methanone.

4. The compound of claim 2, selected from the group consisting of
{(3SR,4RS)-3-(3,4-dichloro-phenyl)-4-[(3-fluoro-4-trifluoromethyl-benzyl)-methyl-amino]-pyrrolidin-1-yl}-(4-imidazol-1-yl-phenyl)-methanone;
{(3SR,4RS)-3-(3,4-dichloro-phenyl)-4-[(3-fluoro-4-trifluoromethyl-benzyl)-methyl-amino]-pyrrolidin-1-yl}-[4-(1,1-dioxo-1-6-isothiazolidin-2-yl)-phenyl]-methanone;
{(3SR,4RS)-3-(3,4-dichloro-phenyl)-4-[(3-fluoro-4-trifluoromethyl-benzyl)-methyl-amino]-pyrrolidin-1-yl}-(4-pyridin-2-yl-phenyl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-pyridin-3-yl-phenyl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-pyridin-4-yl-phenyl)-methanone;
{(3SR,4RS)-3-(3,4-dichloro-phenyl)-4-[(3-fluoro-4-trifluoromethyl-benzyl)-methyl-amino]-pyrrolidin-1-yl}-(4-[1,3,4]oxadiazol-2-yl-phenyl)-methanone;
N-(4-{(3SR,4RS)-3-(3,4-dichloro-phenyl)-4-[(3-fluoro-4-trifluoromethyl-benzyl)-methyl-amino]-pyrrolidine-1-carbonyl}-phenyl)-acetamide;
4-{(3SR,4RS)-3-(4-chloro-3-fluoro-phenyl)-4-[(3-fluoro-4-trifluoromethyl-benzyl)-methyl-amino]-pyrrolidine-1-carbonyl}-benzonitrile;
{(3SR,4RS)-3-(3,4-dichloro-phenyl)-4-[(3-fluoro-4-trifluoromethyl-benzyl)-methyl-amino]-pyrrolidin-1-yl}-(4-oxazol-5-yl-phenyl)-methanone; and
4-{(3SR,4RS)-3-(3,4-dichloro-phenyl)-4-[methyl-(4-trifluoromethyl-benzyl)-amino]-pyrrolidine-1-carbonyl}-benzonitrile.

5. The compound of claim 1, wherein Ar¹ is heteroaryl and Ar² is phenyl.

6. The compound of claim 5, selected from the group consisting of
benzo[1,3]dioxol-5-yl-{(3SR,4RS)-3-(3,4-dichloro-phenyl)-4-[(3-fluoro-4-trifluoromethyl-benzyl)-methyl-amino]-pyrrolidin-1-yl}-methanone;
{(3SR,4RS)-3-(3,4-dichloro-phenyl)-4-[(3-fluoro-4-trifluoromethyl-benzyl)-methyl-amino]-pyrrolidin-1-yl}-(6-methyl-pyridin-3-yl)-methanone;
5-{(3SR,4RS)-3-(3,4-dichloro-phenyl)-4-[(3-fluoro-4-trifluoromethyl-benzyl)-methyl-amino]-pyrrolidine-1-carbonyl}-pyridine-2-carbonitrile;
{(3SR,4RS)-3-(3,4-dichloro-phenyl)-4-[(3-fluoro-4-trifluoromethyl-benzyl)-methyl-amino]-pyrrolidin-1-yl}-(6-morpholin-4-yl-pyridin-3-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(6-fluoro-pyridin-3-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(6-methoxy-pyridin-3-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(6-pyrazol-1-yl-pyridin-3-yl)-methanone;
{(3SR,4RS)-3-(3,4-dichloro-phenyl)-4-[(3-fluoro-4-trifluoromethyl-benzyl)-methyl-amino]-pyrrolidin-1-yl}-(2-methyl-pyridin-4-yl)-methanone;

{(3SR,4RS)-3-(3,4-dichloro-phenyl)-4-[(3-fluoro-4-trifluoromethyl-benzyl)-methyl-amino]-pyrrolidin-1-yl}-(6-hydroxy-pyridin-3-yl)-methanone;
{(3SR,4RS)-3-(3,4-dichloro-phenyl)-4-[(3-fluoro-4-trifluoromethyl-benzyl)-methyl-amino]-pyrrolidin-1-yl}-[1,6]naphthyridin-2-yl-methanone;
{(3SR,4RS)-3-(3,4-dichloro-phenyl)-4-[(3-fluoro-4-trifluoromethyl-benzyl)-methyl-amino]-pyrrolidin-1-yl}-(2-methoxy-pyrimidin-5-yl)-methanone;
(3H-benzotriazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone;
(3H-benzoimidazol-5-yl)-{(3SR,4RS)-3-(3,4-dichloro-phenyl)-4-[(3-fluoro-4-trifluoromethyl-benzyl)-methyl-amino]-pyrrolidin-1-yl}-methanone;
4-(5-{(3SR,4RS)-3-(3,4-dichloro-phenyl)-4-[(3-fluoro-4-trifluoromethyl-benzyl)-methyl-amino]-pyrrolidine-1-carbonyl}-pyridin-2-yl)-piperazine-1-carboxylic acid tert-butyl ester; and
{(3SR,4RS)-3-(3,4-dichloro-phenyl)-4-[(3-fluoro-4-trifluoromethyl-benzyl)-methyl-amino]-pyrrolidin-1-yl}-[6-(1,1-dioxo-1-6-thiomorpholin-4-yl)-pyridin-3-yl]-methanone.

7. A pharmaceutical composition comprising a therapeutically effective amount of a compound of formula I

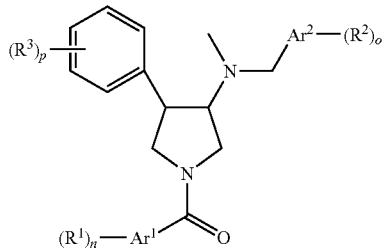

wherein $Ar^1$ is aryl or heteroaryl;

$Ar^2$ is aryl or heteroaryl;

$R^1$ is hydrogen, halogen, hydroxy, lower alkyl, lower alkoxy, lower alkyl substituted by halogen, lower alkoxy substituted by halogen, S-lower alkyl, —S(O)$_2$-lower alkyl, —S(O)$_2$-di-lower alkyl amino, cyano, amino, mono or di-lower alkyl amino, C(O)-lower alkyl, NHC(O)-lower alkyl, cycloalkyl, heterocyclyl, or heteroaryl optionally substituted by lower alkyl;

$R^2$ is hydrogen, halogen, lower alkyl, lower alkoxy, lower alkyl substituted by halogen or cyano;

$R^3$ is hydrogen, halogen, lower alkyl or lower alkyl substituted by halogen;

n is 1, 2 or 3; wherein when n is 2 or 3, each $R^1$ is the same or different;

o is 1, 2 or 3; wherein when o is 2 or 3, each $R^2$ is the same or different; and p is 1, 2 or 3; wherein when p is 2 or 3, each $R^4$ is the same or different;

or a pharmaceutically active salt, a racemic mixture, an enantiomer, an optical isomer or a tautomeric form thereof and a pharmaceutically acceptable carrier.

* * * * *